(12) United States Patent
Di Carlo et al.

(10) Patent No.: US 10,717,086 B2
(45) Date of Patent: Jul. 21, 2020

(54) INTEGRATED SYSTEM FOR ISOLATION AND EMULSIFICATION OF PARTICLES AND CELLS

(71) Applicant: The Regents of the University of California, Oakland, CA (US)

(72) Inventors: Dino Di Carlo, Los Angeles, CA (US); Manjima Dhar, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 315 days.

(21) Appl. No.: 15/690,046

(22) Filed: Aug. 29, 2017

(65) Prior Publication Data
US 2018/0056294 A1 Mar. 1, 2018

Related U.S. Application Data

(60) Provisional application No. 62/380,890, filed on Aug. 29, 2016.

(51) Int. Cl.
*B01L 3/00* (2006.01)
*G01N 33/543* (2006.01)
*B01J 19/00* (2006.01)

(52) U.S. Cl.
CPC ... *B01L 3/502792* (2013.01); *B01L 3/502761* (2013.01); *B01L 3/502784* (2013.01);
(Continued)

(58) Field of Classification Search
CPC ............. B01L 3/502792; B01L 3/00; B01L 2400/0478; B01L 3/502784;
(Continued)

(56) References Cited

U.S. PATENT DOCUMENTS 7,803,599 B2 9/2010 Lutz et al.
9,005,455 B2 4/2015 Achard et al.
(Continued)

FOREIGN PATENT DOCUMENTS

WO    WO 02/092222 A2    11/2002
WO    WO 2008/157257 A1   12/2008
WO    WO 2010/036912 A2    4/2010

OTHER PUBLICATIONS

Bhagat, Ali Asgar S. et al., Pinched flow coupled shear-modulated inertial microfluidics for high-throughput rare blood cell separation, Lab Chip, 2011, 11, 1870-1878.
(Continued)

*Primary Examiner* — Rebecca M Fritchman
(74) *Attorney, Agent, or Firm* — Vista IP Law Group LLP

(57) ABSTRACT

A system for isolating and emulsifying particles or cells within droplets includes a microfluidic trapping device having an inlet and an outlet and one or more channels disposed between the inlet and the outlet, at least some of the one or more channels having a plurality of expansion regions serially arranged along the length thereof. A droplet generation device is fluidically coupled to the outlet of the microfluidic trapping device, the droplet generation device has a plurality of channels of a first height that terminate at an interface into a chamber having a second height that is greater than the first height, wherein the plurality of channels droplet generation device and the chamber contain an oil phase therein and wherein the interface is a step junction. In some embodiments, the droplet generation device is itself oriented at an angle with respect to horizontal to prevent droplet coalescence.

12 Claims, 14 Drawing Sheets

(52) U.S. Cl.
CPC ......... *G01N 33/54333* (2013.01); *B01J 19/00* (2013.01); *B01J 2219/0034* (2013.01); *B01L 3/00* (2013.01); *B01L 2200/0652* (2013.01); *B01L 2200/0668* (2013.01); *B01L 2300/0816* (2013.01); *B01L 2400/0478* (2013.01)

(58) Field of Classification Search
CPC ..... B01L 2200/0652; B01L 2200/0668; B01L 2300/0816; B01L 3/502761; G01N 33/54333; B01J 2219/0034; B01J 19/00
See application file for complete search history.

(56) References Cited

U.S. PATENT DOCUMENTS

| | | | |
|---|---|---|---|
| 9,133,499 B2* | 9/2015 | Di Carlo | B01L 3/502746 |
| 2005/0048581 A1* | 3/2005 | Chiu | B01L 3/502761 |
| | | | 435/7.1 |
| 2008/0009780 A1 | 1/2008 | Leonard et al. | |
| 2008/0318324 A1 | 12/2008 | Chiu et al. | |
| 2009/0014360 A1 | 1/2009 | Toner et al. | |
| 2009/0286300 A1 | 11/2009 | Le Vot et al. | |
| 2010/0247492 A1 | 9/2010 | Kuhn et al. | |
| 2010/0279321 A1 | 11/2010 | Chin et al. | |
| 2011/0070581 A1 | 3/2011 | Gupta et al. | |
| 2011/0096327 A1 | 4/2011 | Papautsky et al. | |
| 2011/0117577 A1 | 5/2011 | Reboud et al. | |
| 2015/0355060 A1 | 12/2015 | Di Carlo et al. | |
| 2016/0139015 A1 | 5/2016 | Di Carlo et al. | |
| 2019/0134633 A1* | 5/2019 | Bharadwaj | G01N 1/28 |

OTHER PUBLICATIONS

Cristofanilli, Massimo et al., Circulating Tumor Cells: A Novel Prognostic Factor for Newly Diagnosed Metastatic Breast Cancer, Journal of Clinical Oncology, vol. 23, No. 7 (Mar. 1, 2005), pp. 1420-1430.
Lin, Cheng Ming et al., Trapping of Bioparticles via Microvortices in a Microfluidic Device for Bioassay Applications, Anal. Chem. 2008, 80 (23), pp. 8937-8945.
Nagrath, Sunitha et al., Isolation of rare circulating tumour cells in cancer patients by microchip technology, Nature 450, 1235-1239 (Dec. 20, 2007).
Moon, Hui-Sung et al., Continuous separation of breast cancer cells from blood samples using multi-orifice flow fractionation (MOFF) and dielectrophoresis (DEP), Lab Chip, 2011, 11, 1118-1125.
Park, Jae-Sung et al., Continuous focusing of microparticles using inertial lift force and vorticity via multi-orifice microfluidic channels, Lab Chip, 2009, 9, 939-948.
Stott, Shannon L. et al., Isolation of circulating tumor cells using a microvortex-generating herringbone-chip, Center of Engineering in Medicine, Massachusetts General Hospital, Harvard Medical School, Boston, MA 02114, USA, PNAS, Oct. 26, 2010, vol. 107, No. 43, pp. 18392-18397.
Sethu, Palaniappan et al., Microfluidic Isolation of Leukocytes from Whole Blood for Phenotype and Gene Expression Analysis, Anal. Chem., 2006, 78(15), pp. 5453-5461.
Hur, Soojung Claire et al., High-throughput size-based rare cell enrichment using microscale vortices, Biomicrofluidics, vol. 5(2), pp. 22206-01-22206-10 (Jun. 29, 2011).
Mach, Albert J. et al., Continuous Scalable Blood Filtration Device Using Inertial Microfluidics, Biotechnology and Bioengineering, vol. 107, No. 2, Cotber 1, 2010, pp. 302-311.
Park, Jae-Sung et al., Multiorifice Flow Fractionation: Continuous Size-Based Separation of Microspheres Using a Series of Contraction/Expansion Microchannels, Anal. Chem. 2009, 81, pp. 8280-8288.
PCT International Search Report for PCT/US2011/051224, Applicant: The Regents of the University of California, Form PCT/ISA/210 and 220, dated Apr. 18, 2012 (4pages).

PCT Written Opinion of the International Search Authority for PCT/US2011/051224, Applicant: The Regents of the University of California, Form PCT/ISA/237, dated Apr. 18, 2012 (4pages).
PCT International Preliminary Report on Patentability (Chapter I of the Patent Cooperation Treaty) for PCT/US2011/051224, Applicant: The Regents of the University of California, Form PCT/IB/326 and 373, dated Mar. 28, 2013 (6pages).
Patent Examination Report No. 1, dated Jul. 15, 2014, in Australian Patent Application No. 2011302302, Application: The Regents of the University of California (10pages).
Chiu, D.T., Cellular manipulations in microvortices, Anal Bioanal Chem (2007) 387:17-20.
Khabiry, M. et al., Cell Docking in Double Grooves in a Microfluidic Channel, NIH Public Access Author Manuscript, 2009, [Retrieved on Feb. 13, 2014]. Retrieved from the Internet <URL:http://www.ncbi.nih.gov/pmc/articles/PMC2683980/> published in final edited form as: Small, 5(10):1186-1194.
Lee, M.G. et al., Three-dimensional hydrodynamic focusing with a single sheath flow in a single-layer microfluidic device, Lab on a Chip, 2009, 9(21):3155-3160.
Lettieri, G.L, et al., A novel microfluidic concept for bioanalysis using freely moving beads trapped in recirculating flows, Lab on a Chip, 2003, 3(1):34-39.
Shelby, J.P., et al, High radial acceleration in microvortices, Nature, 2003, 425:38.
Notification of the First Office Action including an English translations prepared by Kangxin Partners, P.C.dated Feb. 17, 2014, in Chinese Patent Application No. 201180044092.8 Application: The Regents of the University of California (16pages).
Notification of the Second Office Action including an English translations prepared by Kangxin Partners, P.C. dated Aug. 5, 2014, in Chinese Patent Application No. 201180044092.8 Application: The Regents of the University of California (8pages).
Moon, H.S. et al., Continuous Separation of Breast Cancer Cells from Blood using Multi-Stage Multi-Orifice Flow Fractionation (MS-MOFF), 15th International Conference on Miniaturized Systems for Chemistry and Life Sciences, Oct. 2-6, 2011, Seattle, Washington, USA, pp. 1218-1220.
Stott, Shannon et al., Isolation of circulating tumor cells using a microvortex-generating herringbone-chip, PNAS, Oct. 26, 2010, vol. 107, No. 43, 18392-18397.
Notice of Acceptance dated Nov. 26, 2014 in Australian Patent Application No. 2011302302, Applicant: The Regents of the University of California (3pages).
Karino et al., 1977. Flow Behaviour of Blood Cells and Rigid Spheres in an Annular Vortex. Philosophical Transactions of the Royal Society of London. Series B, Biological Sciences, vol. 279, No. 967, pp. 413-445.
Gossett et al. 2010. Label-free cell separation and sorting in microfluidic systems. Analytical and Bioanalytical Chemistry, vol. 397, pp. 3249-3267.
Bergman et al. 1995-2006. Anatomy Atlases, A digital library of anatomy information, 9 pages.
Hsu et al. 2008. Microvortex for focusing, guiding and sorting of particles. Lab on a Chip, vol. 8, pp. 2128-2134.
Sower, Elodie et al., Passive microfluidic devices for plasma extraction from whole human blood, Sens. Actuators B: Chem. (2009), doi:10.1016/j.snb.2009.05.023.
Sollier, Elodie et al., Fast and continuous plasma extraction from the whole human blood based on expanding cell-free layer devices, Biomed Microdevices (2010) 12:485-497.
Notice of Rejection dated Sep. 29, 2015 in Japanese Patent Application No. 2013-528369, Applicant: The Regents of the University of California, (3pges).
First Office Action dated Jan. 19, 2016 in Chinese Patent Application No. 2015100887109, Applicant: The Regents of the University of California, (16pgs).
Extended European Search Report (EESR) dated Apr. 4, 2016 in European Patent Application No. 118257385, Applicant: The Regents of the University of California, (7pgs).
Patent Examination Report No. 1 dated Jan. 15, 2016 in Australian Patent Application No. 2015200910, Applicant: The Regents of the University of California, (5pgs).

(56) References Cited

OTHER PUBLICATIONS

Patent Examination Report No. 2 dated Apr. 4, 2016 in Australian Patent Application No. 2015200910, Applicant: The Regents of the University of California, (3pgs).

Notice of Acceptance dated Sep. 7, 2016 in Australian Patent Application No. 2015200910, Applicant: The Regents of the University of California, (1pg).

Communication pursuant to Article 94(4) EPC dated Nov. 23, 2016 in European Application No. 11 825 738.5-1371, Applicant: The Regents of the University of California (3pages).

Dangla, Remi et al., Droplet microfluidics driven by gradients of confinement, PNAS, Jan. 15, 2013, vol. 110, No. 3, 853-858.

Jing, T. et al., High-Throughput Single Cell Protease Analysis on Human Circulating Tumor Cells, 19th International Conference on Miniaturized Systems for Chemistry and Life Sciences, Oct. 25-29, 2015, Gyeongju, Korea, pp. 490-492.

Yeo, Trifanny et al., Microfluidic enrichment for the single cell analysis of circulating tumor cells, Scientific Reports, 6:22076, DOI: 10.1038/srep22076; published: Feb. 29, 2016.

Kumaresan, Palani et al., High-Throughput Single Copy DNA Amplification and Cell Analysis in Engineered Nanoliter Droplets, Anal. Chem. 2008, 80, 3522-3529.

\* cited by examiner

INTEGRATED SYSTEM FOR ISOLATION AND EMULSIFICATION OF PARTICLES AND CELLS

RELATED APPLICATION

This Application claims priority to U.S. Provisional Patent Application No. 62/380,890 filed on Aug. 29, 2016, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with Government support under CA177456, awarded by the National Institutes of Health. The Government has certain rights in the invention.

TECHNICAL FIELD

The technical field generally relates to microfluidic devices that are used to selectively isolate or trap particles and/or cells followed by subsequent emulsification into droplets or small reaction volumes.

BACKGROUND

CTCs obtained through liquid biopsies show promise as a tool for studying primary and metastatic tumors. CTCs open access to the genetic makeup and protein architecture of the primary and secondary tumors without an invasive biopsy. The identification of CTCs enables physicians to better diagnose specific cancer types or stages as well as tailor treatment protocols specific to a particular patient. These cells are rare in the blood and they range from 1-100 CTCs/ml of whole blood. Challenges in isolating the CTCs involve processing large volumes of blood in a time effective manner and concentrating cells of interest into manageable volumes for analysis. Additionally, in order to perform cost-effective genomic analysis, highly pure samples are needed with low background noise from white blood cells. Immunomagnetic bead-based separation of CTCs generally uses EpCAM antibodies; however this technique misses any CTCs which have undergone Epithelial to Mesenchymal Transition due to EpCAM down regulation. Existing CTC isolation technologies that rely on physical properties of CTCs such as size based filtration, acoustic wave deflection, dielectrophoresis and size based inertial separation are still limited in throughput, pre-processing steps such as RBC-lysis and low sample purity.

More recently, a microfluidic-based device called the Vortex Chip (Vortex Biosciences, Inc., Menlo Park, Calif.) has demonstrated an ability to use high throughput inertial microfluidics and microscale vortices to passively enrich large cells such as CTCs at high purity from large volumes of blood. This same Vortex Chip device is able to capture and enrich beads. The Vortex Chip device captures CTCs (or large particles such as beads) using a series of specially-designed expansion regions that are serially arranged along one or more microfluidic channels. Vortices are generated within the expansion regions and can be used to selectively isolate or trap CTCs or beads from a fluid flow containing the same. For example, U.S. Pat. No. 9,133,499 describes a method and device for isolating cells from a heterogeneous solution using microfluidic trapping vortices. The trapped CTCs and/or beads can be later released from the Vortex Chip for downstream processing or analysis.

Various microfluidic devices for the capture of cells have also been developed. For example, U.S. Patent Application Publication No. 2012-0125842 describes a microfluidic system for the encapsulation of elements including cells that uses two immiscible phases to create capsules or droplets that contain cells. Another example is disclosed in U.S. Pat. No. 8,263,023 which discloses a microfluidic-based system for the sorting and automated encapsulation of cell clusters such as islets of Langerhans. Moreover, while cell encapsulation using emulsions has been performed, this has required the use of a separate immiscible phase co-flow system to create the droplets. This makes the system more complicated and increases the costs for additional pumps, valves, and the like. In addition, other droplet generation devices have used complicated angled structures that are difficult to manufacture in microfluidic devices such as that disclosed in Dangla et al., Droplet microfluidics driven by gradients of confinement, PNAS, vol. 110, no. 3 853-58 (2013).

SUMMARY

According to one aspect of the invention, a microfluidic trapping device such as a Vortex Chip device is integrated with a downstream droplet or emulsification generation device. Trapped particles (e.g., beads) or cells within the microfluidic trapping device are released from the expansion regions whereby the particles or cells are then entrained within small emulsification volumes such as droplets. Notably, the trapped particles or cells can be exposed to reagents or reactants or wash solutions. In this manner, solution exchange may be performed, as appropriate, when the particles or cells are in the trapped state within the microfluidic trapping device. The particles and cells can then be released in a new reaction solution and encapsulated within the emulsification volumes. The small reaction volumes can contain reagents, reactants, molecules, substrates, and like that can then be incubated with the cells or beads. In this regard, the emulsification volumes or droplets can form individual reaction volumes that can be monitored using, for example, fluorescent imaging or other fluorescent particle detection approaches such as flow cytometry. Fluorescent imaging can be used to identify particular cells that may be trapped or target species, such as biomolecules like nucleic acids and proteins, contained within the sample (e.g., a blood sample or other biological sample).

The downstream droplet or emulsification generation device, in one embodiment, includes a plurality of feed channels that empty into a larger reservoir or chamber that has a stepped increase in height (i.e., step junction) as compared to the height of the feed channels. In one embodiment, the step meets the channel at around a 90° angle (i.e., a substantially vertical step). The droplets can accumulate in the reservoir or chamber. The droplet generation device includes an oil phase (with optional surfactant) contained therein through which the aqueous-based flow enters from the microfluidic trapping device. Aqueous droplets are formed at the interface between the narrow channels and stepped-up reservoir. The aqueous droplets are buoyant relative to the oil phase and rise at the droplet generation region. In one aspect, the droplet generation region of the droplet generation device is angled relative to horizontal so as to allow generated drops to rise away from the narrow feed channels and prevent the droplets from coalescing together. In this design, as opposed to other microfluidic droplet generators, while there is an oil phase contained in the droplet generation device, there is no need to co-flow oil with an aqueous flow to generate droplets. This is important to allow generation of many droplets quickly without jetting and in a simple design that does not have extra pumps or valves or 3D fluid routing that is required for co-flow or T-junction based droplet generators.

In one embodiment, the droplet generator has a number of channels that outflow to the reservoir or chamber with the larger height for droplet formation. Importantly, the droplet reservoir or chamber may be formed with a flat or level top or roof such that standard microfluidic manufacturing methods can be made to form the device. There is no need for an angled roof as disclosed to be necessary in Dangla et al. to drive surface-tension driven motion of droplets because the entire droplet generator device can be angled relative to horizontal or situated in a vertical direction to make use of buoyant forces to drive droplet motion. The droplet generator may have branched channels that make it highly parallelized so that it can split the high flow rate from the microfluidic trapping device during the release step. If the flow is not split, the droplet generator does not function properly; leading to jetting of flow or less uniform droplet size, which prevents facile calibration of measured signals between droplets.

In one alternative embodiment, the channels in the droplet generation device transition to a terraced region prior to interfacing with the reservoir or chamber having the higher height than the feeding channels. The terraced region may be formed by increasing the width of the feed channels prior to interfacing with the reservoir or chamber. It has been found that the presence of the terraced region may provide better control of the size of the droplets created by the droplet generation device.

In one aspect of the invention, individual cells are trapped within the microfluidic trapping device, washed, and a probe (e.g., fluorescence resonance energy transfer—FRET probe) for matrix metalloproteinases (MMPs) is introduced, and then released along with the FRET probe for matrix metalloproteinases. The FRET probe is used to assay protease secretion from individual cancer cells and becomes fluorescent when proteases act on the peptide bonds in the probe. The cells plus the FRET probe are captured within the small droplet volumes. Each small droplet which has a volume of a few nanoliters acts as a small reaction volume that accumulates fluorescent product at high concentration. This is beneficial in that the measured signal from the droplet (e.g., emitted fluorescent light) has a high signal-to-noise ratio, because the effective concentration of released proteases in the droplet and effective concentration of cleaved FRET probes remains high in the small droplet volume. The droplets that are generated in the system can be collected and then imaged with a fluorescent imaging device. Of course, other FRET-probes that include cleavage sites that are susceptible to other enzyme classes (e.g., esterases, hyaluronidases, amylases, etc.) and known in the art could also be used to assay other enzyme levels at the single-cell level.

In another aspect of the invention, particles such as beads or the like are trapped within the microfluidic trapping device. The beads may have one or more biomarkers or chemical moieties bound to the surface thereof that are selective to a particular target. Biomarkers or chemical moieties may include, for example, nucleic acids, proteins, or exosomes/microvesicles.

In another embodiment, a system for isolating and emulsifying particles or cells within droplets includes a microfluidic trapping device having an inlet and an outlet and one or more channels disposed between the inlet and the outlet, at least some of the one or more channels having a plurality of expansion regions serially arranged along the length thereof. The system further includes a droplet generation device fluidically coupled to the outlet of the microfluidic trapping device, the droplet generation device comprising a plurality of channels of a first height that terminate at an interface into a chamber having a second height that is greater than the first height, wherein the plurality of channels of the droplet generation device and the chamber contain an oil phase therein.

In another embodiment, a method of using the system described above includes flowing a fluid sample containing cells through the microfluidic trapping device, wherein at least some of the cells are trapped within the expansion regions; flowing one or more reactants or reagents through the microfluidic trapping device; releasing the cells trapped within expansion regions; and generating droplets containing the released cells and reactant or reagents with the droplet generation device.

In another embodiment, a method of using the system described above includes flowing a fluid sample through the microfluidic trapping device containing biomarker-bearing particles, wherein at least some of the particles are trapped within the expansion regions; flowing a wash solution through the microfluidic trapping device; flowing one or more reactants or reagents through the microfluidic trapping device; releasing the trapped particles from the expansion regions; and generating droplets containing the released particles and reactants or reagents with the droplet generation device.

BRIEF DESCRIPTION OF THE DRAWINGS

FIG. 13 illustrates how MMP release and substrate conversion increases over time. Signal increase over time can be measured through fluorescence microscopy, flow cytometry, or imaging cytometry of the droplets. Empty droplets do not show signal above the background levels.

DETAILED DESCRIPTION OF THE ILLUSTRATED EMBODIMENTS

Figure 1:
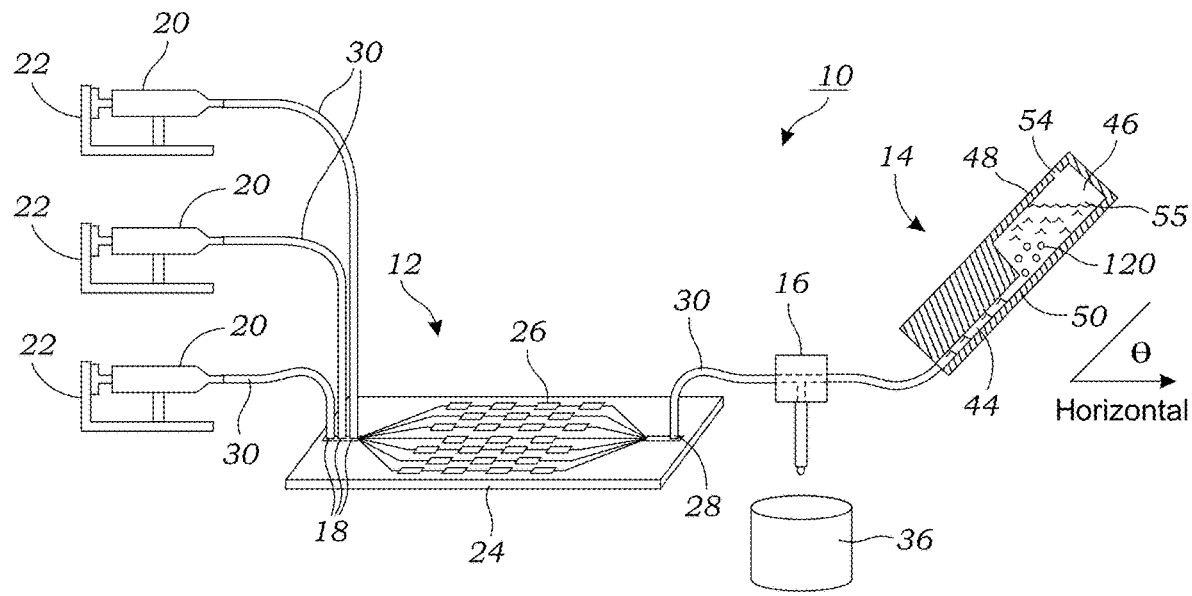
FIG. 1 illustrates a system for isolating and emulsifying particles or cells within droplets according to one embodiment.
Figure 2:
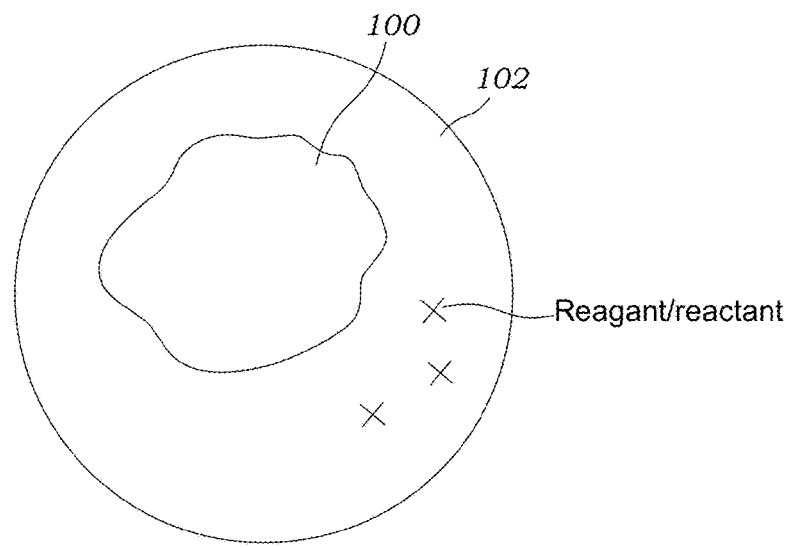
FIG. 2 illustrates a droplet containing a cell.

FIG. 1 illustrates a system 10 for isolating and emulsifying particles or cells 100 within droplets 120 (as seen, e.g., in FIG. 2) according to one embodiment. The system 10 includes several main sub-components including an upstream located microfluidic trapping device 12, a downstream located droplet generation device 14, and a valve 16 interposed between the output from the microfluidic trapping device 12 and the droplet generation device 14. As seen in FIG. 1, the microfluidic trapping device 12 includes one or more inlets 18 that are coupled to one or more fluid sources 20. The fluid sources 20 may include, for example, a sample fluid, a wash fluid, buffer fluid, a fluid containing one or more reagents or reactants, fluid containing particles or cells 100, and the like. In one embodiment, the fluid source 20 includes a sample fluid obtained from a mammalian subject that includes cells 100. The fluid sources 20 are delivered to the system 10 via one or more pumps 22. The one or more pumps 22 may include a syringe pump, peristaltic pump, pressure source or the like that is commonly used in connection with microfluidic devices. As seen in FIG. 1, the fluid source 20 is contained in a syringe that is mounted with syringe pumps 22. A pressurized source of gas or air can be used to generate the pumping pressure that is used to deliver the fluid source(s) 20 into the microfluidic trapping device 12.

In one preferred aspect of the invention, the microfluidic trapping device 12 is formed in a microfluidic substrate or chip 24 and contains a plurality of microfluidic channels 26 that are coupled to the one or more inlets 18 at one end. The microfluidic channels 26 are fluidically coupled to an outlet 28. The one or more inlets 18 may be coupled to the pump(s) 22 using tubing 30. Similarly, tubing 30 may be coupled to the outlet 28 of the microfluidic substrate or chip 24. The microfluidic substrate or chip 24 is typically made using standard photolithography or other techniques used to form microfluidic devices. The microfluidic substrate or chip 24 may be made of any number of materials for the substrate such as, for example, silicon, glass, polymers or plastics (e.g., cyclic olefin polymer (COP), cyclic olefin copolymer (COC), polycarbonate (PC), poly(methyl methacrylate) (PMMA), polydimethylsiloxane (PDMS)).

Figure 3:
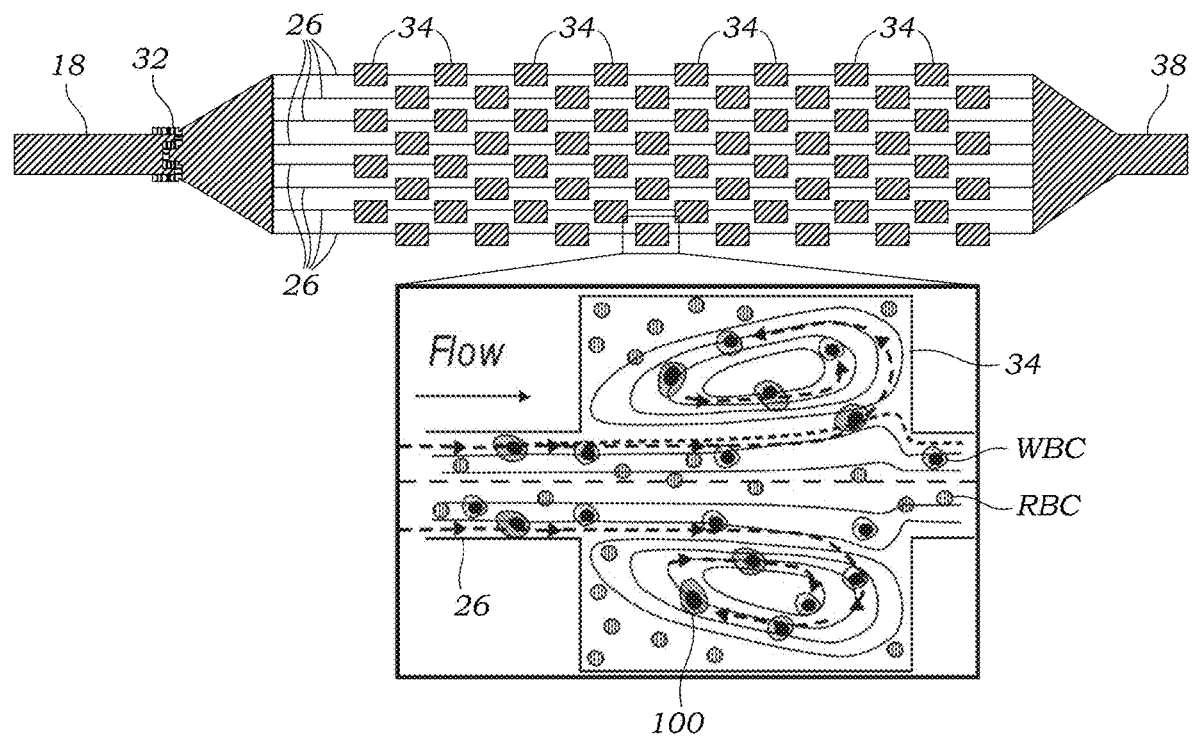
FIG. 3 illustrates one embodiment of a microfluidic trapping device.

In one particular embodiment, as seen in FIG. 3, there are eight (8) separate microfluidic channels 26 that are each coupled at a respective upstream end to a common inlet 18 although a different number of microfluidic channels 26 can be used as well. The inlet 18 may contain an optional filter 32 that is used to filter out larger particles or other contaminants which would tend to clog the microfluidic trapping device 12 during operation. As best seen in FIG. 3, each microfluidic channel 26 has a plurality of expansion regions 34 that are formed along the length of the microfluidic channel 26. The expansion regions 34 are formed by temporary increases in the cross-sectional dimension of the microfluidic channel 26. In one particular embodiment, the width cross-sectional dimension is increased to form the expansion regions 34 while the height cross-sectional dimension remains the same. Of course, the height dimension and/or the width dimension may be increased to form the expansion regions 34. As seen in FIG. 3, the expansion regions 34 are formed following an upstream region of the microfluidic channels 26 that is free of expansion regions 34. In one embodiment, this upstream region that is free of expansion regions 34 may have a length that varies but is generally around 500 μm in length to allow the flow profile to fully develop. Following the upstream region of the microfluidic channel 26, each separate microfluidic channel 26 has, in this particular embodiment, eight (8) expansion regions 34 serially arranged along the length of the microfluidic channel 26 although different numbers of expansion regions 34 can also be employed. Each separate expansion region 34 may be separated by a similar distance such as around 500 μm. After the expansion regions 34, the microfluidic channels 26 communicate with a common outlet 28. The dimensions of the expansion regions 34 may vary. In one particular embodiment, the expansion regions include a width of 576 μm (measured across the entire width) and a length of 864 μm (measured across the entire length of the expansion region). The width of the microfluidic channel 26 leading to and from the expansion regions 34 is 24 μm. The height of the microfluidic channel 26 and expansion regions 34 is 44 μm. In another embodiment which uses the Vortex HT Chip, the dimensions of the expansion region 34 may include a width of 480 μm (measured across the entire width) and a length of 720 μm (measured across the entire length of the expansion region). The width of the microfluidic channel 26 leading to and from the expansion regions 34 is 40 μm. The height of the channel and expansion regions is 70 μm. It should be understood that dimensions different from those specifically mentioned above may be used.

The expansion regions 34 of the microfluidic trapping device 12 are used to temporarily trap particles or cells 100 therein. When a fluid containing the particles or cells 100 are flowed through microfluidic trapping device 12, vortices are created in the expansion regions 34 as seen in FIG. 3. The vortices that are formed within the expansion regions stably trap certain-sized particles or cells 100. For example, in one particular embodiment, particles or cells 100 having a diameter or largest dimension that is >10 μm are stably trapped within the expansion regions 34 while smaller particles and cells 100 are not stably trapped within the vortices and continue to flow through the microfluidic channels 26. FIG. 3 illustrates, for example, CTC cells 100 that are stably trapped while white blood cells (WBCs) and red blood cells (RBCs) are not stably trapped and continue to flow down the microfluidic channel 26. In this regard, certain sub-populations of particles or cells 100 may be selectively trapped within the expansion regions 34. These trapped particles or cells 100 may then be exposed to various fluids or solutions that are run through the microfluidic trapping device 12 while maintaining the trapped particles or cells. These include wash or buffer fluids as well as fluids that contain reagents or reactants or labels. Fluid exchange can thus take place within the microfluidic trapping device 12 to selectively expose particles or cells 100 to differing fluids.

Figure 5:
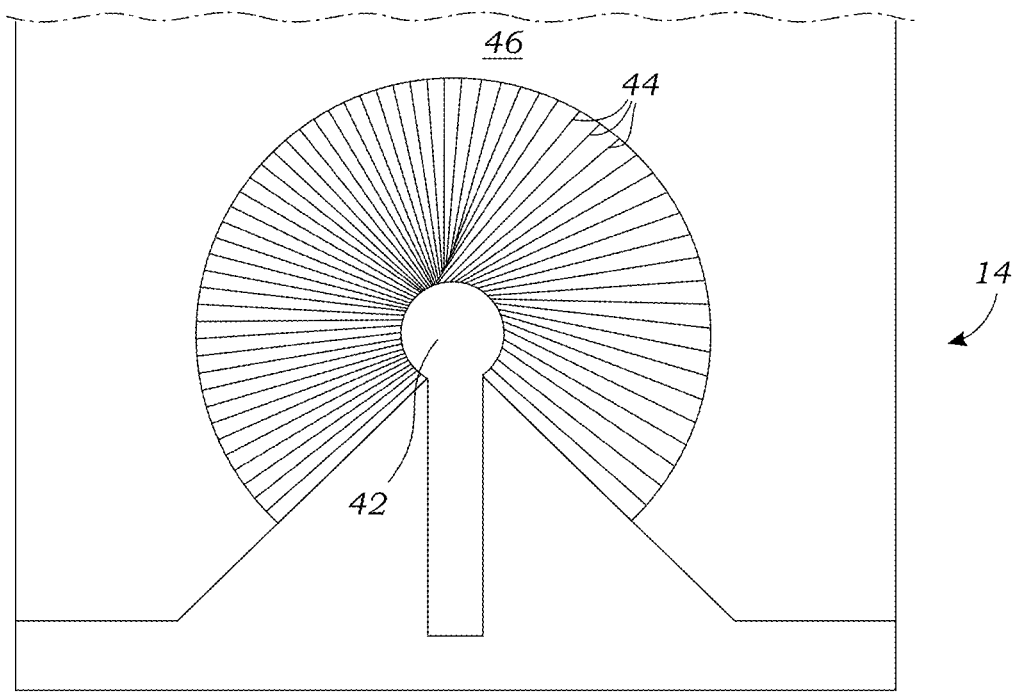
FIG. 5 illustrates one embodiment of a microfluidic-based droplet generation device.

Referring back to FIG. 1, the outlet 28 is coupled to tubing 30 that connects to a valve 16. The valve 16 may be a manually operated valve (e.g., pinch valve) or the valve 16 may be an automatically actuated valve (e.g., pneumatic valve or the like) that is controlled via a computer or controller (not shown). The valve 16 is used to shunt fluid (and any entrained particles or cells 100) to either a waste or other container 36 or pass the fluid to the droplet generation device 14. Various connectors used in connection with microfluidic devices may be used to connect the tubing 30 to the valve 16 and the droplet generation device 14. The droplet generation device 14 is also formed as a microfluidic substrate or chip 40. The droplet generation device 14, according to one embodiment as seen in FIG. 5, has a large expansion region 42 to slow down the relatively fast flow from the microfluidic trapping device 12, and splits into a plurality of microfluidic channels 44 (e.g., seventy-five (75)) before expanding into the reservoir region 46 where droplets 120 accumulate. This device does not split the flow entirely evenly; due to the higher flow rates, droplets from the central microfluidic channels 44 are larger than the droplets 120 from the side located microfluidic channels 44.

Figure 4:
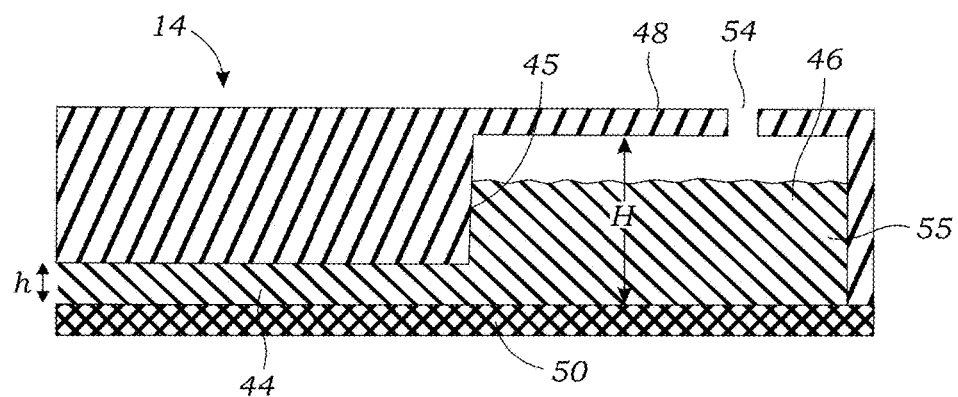
FIG. 4 illustrates a cross-sectional view of a droplet generation device according to one embodiment.
Figure 6:
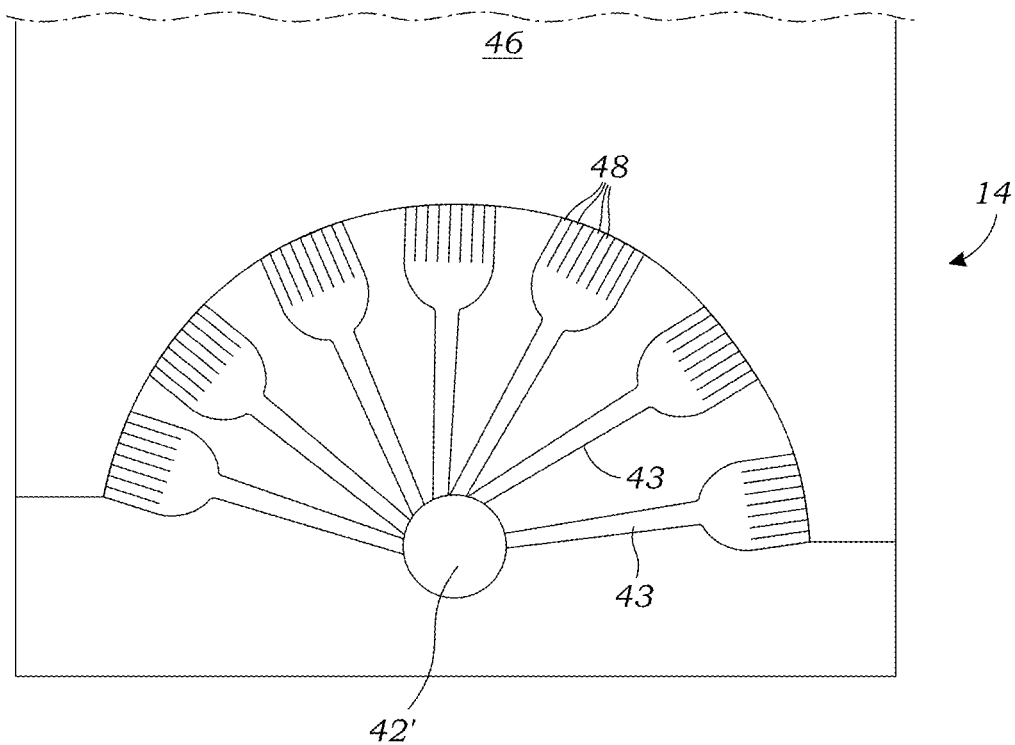
FIG. 6 illustrates another embodiment of a microfluidic-based droplet generation device.

FIG. 6 illustrates another version of the droplet generation device 14. This design distributes the flow rate more evenly among the one hundred (100) microfluidic channels 44. The number of microfluidic channels 44 may vary but is typically within the range of about fifty (50) channels to about two hundred (200) microfluidic channels 44 so that flow rates can be properly matched to prevent jetting of the flow in the droplet generation device 14 at the overall release flow rates of the microfluidic trapping device 12. In this embodiment, there also is a smaller expansion region 42' that includes a number of branch channels 43 that extend therefrom before the narrower feeding microfluidic channels 44, such that cells or particles (e.g., beads) will not become immobilized at the entrance. In the embodiment of FIGS. 5 and 6, the height of the microfluidic channels 44 is around 30-50 μm. The length of these microfluidic channels 44 is on the order of about 1,000 μm. These channels lead to a reservoir or chamber 46 with a larger height of 200 μm. At the interface formed between the end of the feeding microfluidic channels 44 and the reservoir or chamber 46 is where droplet generation takes place. As seen in FIG. 4, a step junction 45 or a vertical transition from the lower height of the microfluidic channels 44 to the higher height of the reservoir or chamber 46 is formed. This step junction 45 is angled about 90° relative to the bottom surface of the droplet generation device 14. The multi-height design of the droplet generation device 14 may be fabricated using double exposure photolithography as explained herein.

The reservoir or chamber 46 is defined by a top surface 48 and a bottom surface 50 that are separated by a height (H) as seen in FIG. 4, with this height being larger than the height (h) of the feeding microfluidic channels 44. In some embodiments, both the top surface 48 and the bottom surface 50 are flat so that the height within the reservoir or chamber 46 is substantially constant along the length or width of the reservoir or chamber 46. This "flat" structure that is used in the droplet generation device 14 facilitates easy manufacturing of the same. There is no need for complex angled top or roof structures.

Figure 7A:
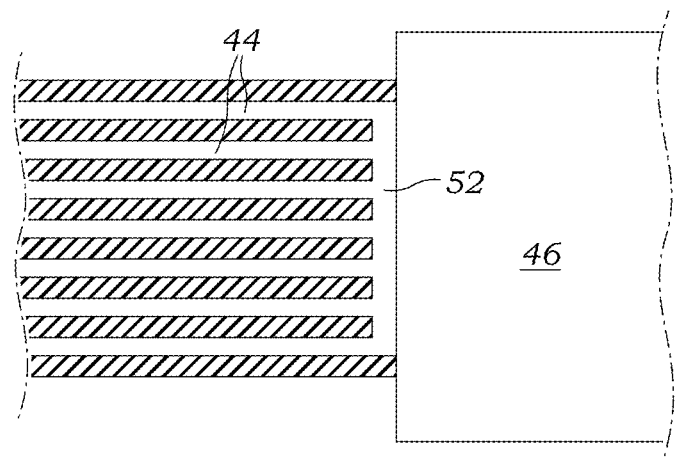
FIG. 7A illustrates one embodiment of the interface formed between the feeding microfluidic channels and the droplet chamber or reservoir. This embodiment illustrated a terraced region.
Figure 7B:
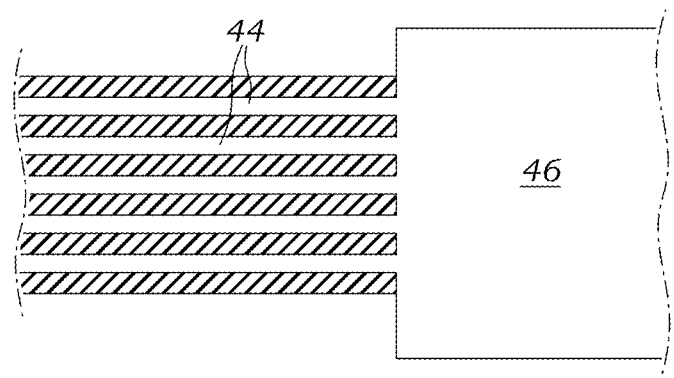
FIG. 7B illustrates one embodiment of the interface formed between the feeding microfluidic channels and the droplet chamber or reservoir. In this embodiment, there is no terraced region.
Figures 8, 9:
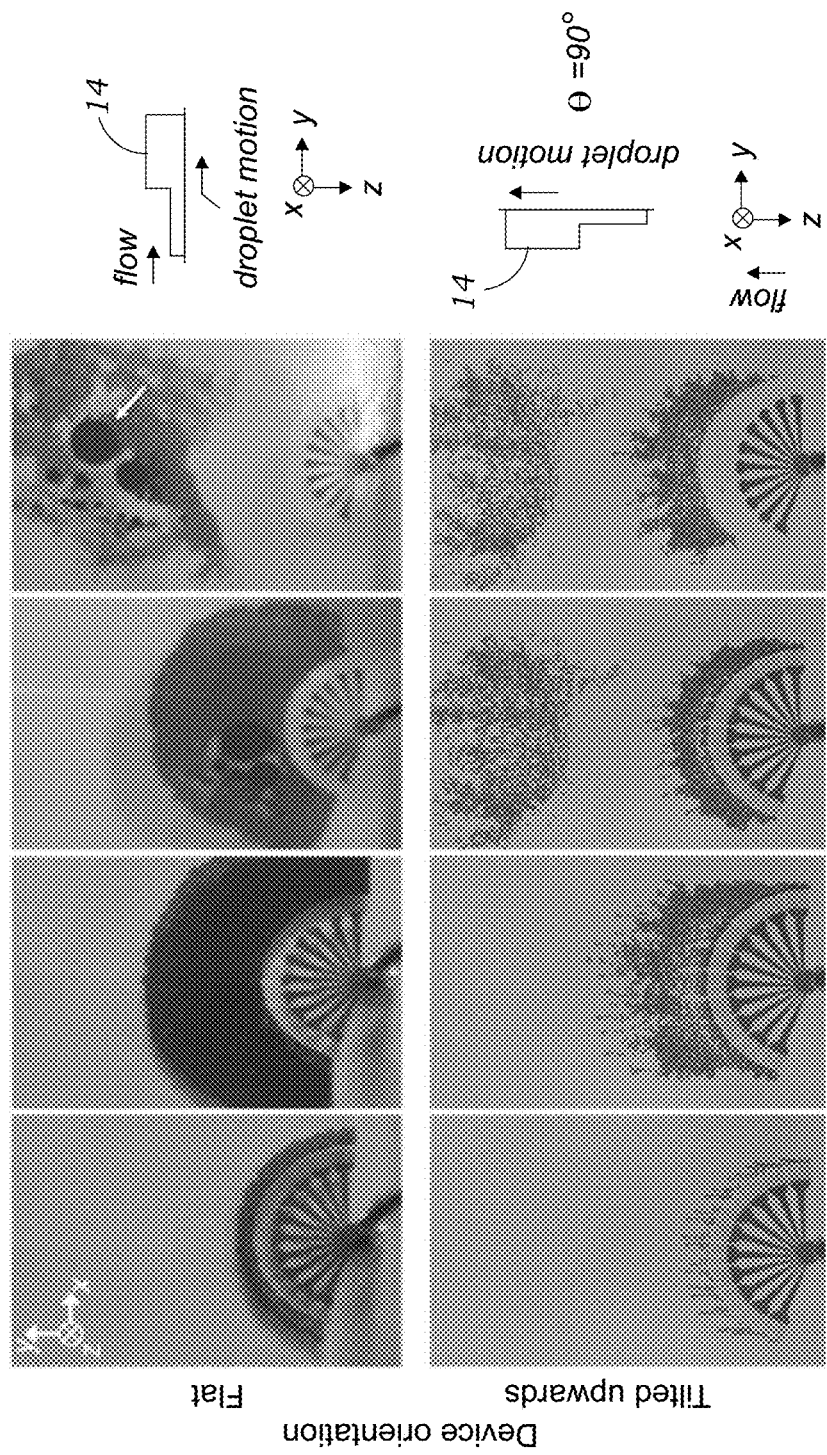
FIG. 8 illustrates the "flat" orientation of the droplet generation device (e.g., with the device oriented in a plane orthogonal to the direction of gravity) alongside photographs illustrating how the droplets do not move away and ultimately coalesce together (white arrow in last panel of images).
FIG. 9 illustrates the tilted or angled orientation with respect to the direction of gravity of the droplet generation device alongside photographs illustrating how the droplets move away from the droplet generating region and do not coalesce together like illustrated in FIG. 8.

In some embodiments, for example as illustrated in FIG. 7, the interface formed between the narrow feed microfluidic channels 44 and the reservoir or chamber 46 may have a terraced region or gap 52 where the side walls in the narrow feed microfluidic channels 44 are removed to form the same. In other embodiments, the terraced region or gap 52 is omitted. FIG. 8 illustrates the same embodiment of FIG. 7 but with the terraced region or gap omitted. Experimentally, embodiments that used the terraced region or gap 52 generate more droplets having more uniform size but is harder to fabricate.

With reference to FIGS. 1 and 4, the reservoir or chamber 46 of the droplet generation device 14 includes an opening or aperture 54. The opening or aperture 54 is used to fill the reservoir or chamber 46 with an oil and/or surfactant mixture 55 as seen in FIG. 1. In addition, the formed droplets 120 can be removed from the reservoir or chamber 46 using the opening or aperture 54. During use, the reservoir or chamber 46 is filled with, for example, 0.5% vol. % Pico-Surf™ surfactant in Novec™ 7500 oil using the opening or aperture 54, although other surfactant and oil solutions can be used. The oil solution is filled to ~50% of the volume of the reservoir or chamber 46; leaving open head space above the oil/surfactant fluid such that when droplets 120 displace the surfactant and oil solution, it will not overflow out of the reservoir or chamber 46. The oil and surfactant mixture can be pre-loaded into the reservoir or chamber 46 using a syringe, pipette, automated dispenser or other mechanism known in the art to dispense small volume of fluids into a cavity, for example approaches developed in the food manufacturing industry could be applied to fill the reservoir or chamber 46 in an automated fashion.

Because there are no additional pumps that are used to drive the flow of the oil/surfactant solution (i.e., the oil/surfactant solution is largely stagnant), the droplet generation device 14, in order to prevent coalescence of the formed droplets 120, should preferably be angled or tilted relative to horizontal. This format is advantageous because no complex fabrication or additional pumping elements are needed to achieve encapsulation of cells or particles 100 into monodisperse droplets 120. In the angled orientation, the buoyancy force on the droplets 120 carries the generated droplets 120 away from the droplet generation zone to prevent coalescence. FIG. 8 illustrates the "flat" orientation of the droplet generation device 14 alongside photographs illustrating how the droplets 120 do not move away and ultimately coalesce together (white arrow). Conversely, as seen in FIG. 9, in the tilted or angled orientation (with positive slope) the droplets 120 spread apart and do not coalesce. The angle θ at which the droplet generation device 100 should be maintained is, in one embodiment, between about 30° and about 90° to manipulate the buoyant droplets 120 away from the channel region into a monolayer at the top surface of the reservoir or chamber 46. Note that these angles of upward tilt are optimal for aqueous-based droplets 120 that are less dense than the oil phase they are suspended in (i.e., the droplets are buoyant). Similar operation for aqueous-based droplets 120 that are denser than the surrounding oil/surfactant phase can be achieved with a downward tilt of the device (e.g., angled between about −30° and about)−90°. This tilting of the droplet generation device 14 is needed to allow for high throughput droplet generation without coalescence given the lack of pumped oil flow. Other designs have used a gradient in height to draw drops away passively due to surface tension effects, however, this is much more difficult to fabricate in microfluidic devices than a single step channel with the device oriented in a tilted arrangement. It should be noted, however that an angled or tilted top surface 48 would also work without having to tilt or angle the droplet generation device 14 although such a structure is much harder to manufacture. Tilting of the droplet generation device 14 may be accomplished by adding one or more shims under the droplet generation device 14 or the base or surface on which the droplet generation device 14 is situated may be tilted at an angle with respect to gravity. The microfluidic trapping device 12 does not need to be tilted or angled although it may operate in a tilted or angled configuration.

In one embodiment, the microfluidic trapping device 12, the droplet generation device 14, and the valve 16 could all be integrated into a single device. For example, the valve 16 could be formed "on-chip" with the microfluidic trapping device 12 and the droplet generation device 14. Alternatively, the components could be assembled and integrated into a single cartridge, housing, or the like.

Figure 10:
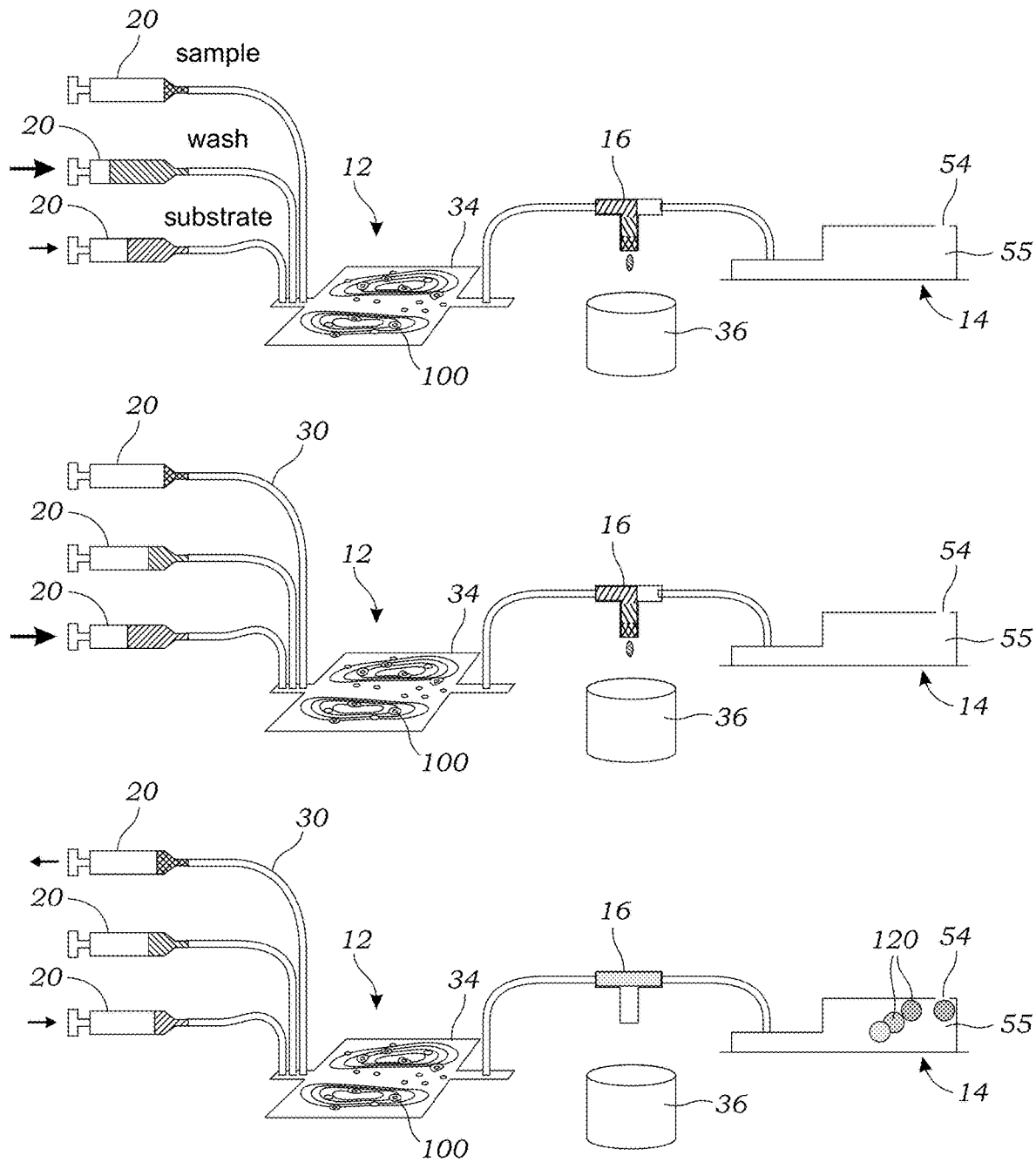
FIG. 10 illustrates an exemplary sequence of operations or steps for the integrated isolation, concentration, and encapsulation of particles or cells into droplets.

FIG. 10 illustrates an exemplary sequence of operations or steps for the integrated isolation, concentration, and encapsulation of particles or cells 100 into droplets 120. In this example, the sample fluid is introduced into the microfluidic trapping device 12 and cells or particles 100 at or above a size cutoff (e.g., 10 μm although the microfluidic trapping device 12 may be tuned for different cutoff sizes) are trapped in the vortices created in the expansion regions 34. Initially, the valve 16 is in a position to direct fluid passing into a waste or other container 36. Smaller particles or cells 100 are not stably trapped and continue flowing through the microfluidic trapping device 12. After the particles or cells 100 are trapped within the expansion regions 34, as seen in operation #1 in FIG. 10, a wash solution is introduced to wash the sample solution from around the particles or cells 100 and wash away smaller particles or cells 100 that are not stably trapped. In addition, reagents or reaction mixes (e.g., the MMP substrate when cells 100 are introduced) are introduced at a low flow rate to prevent back flow into the syringe during this step. In addition, the sample syringe is withdrawn at a low flow rate to prevent pressure build-up in the sample syringe and potential sample pulsing effects which lead to contamination from the sample solution. Next, as seen in operation #2 in FIG. 10, the reagent (e.g., MMP substrate) is input at the same flow rate necessary to maintain the vortices in the expansion regions 34. The flow from the wash source (e.g., syringe) is also stopped. Next, as seen in operation #3 of FIG. 10, the valve 16 that previously diverted flow to a waste container 36 is then switched to divert flow to the droplet generation device 14. The reactant flow rate is lowered and the sample syringe is withdrawn or pulled back (which reduces flow rate through the microfluidic trapping device 12) to release the trapped particles or cells 100 from the vortices. The particles or cells 100 then continue into the droplet generation device 14 and are encapsulated in droplets 120.

The system 10 described herein may also be used in conjunction with particles 100 such as beads that present moieties such as biomarker-binding sites that can bind and/or react with a target. Target biomarkers such as nucleic acids, proteins, or exosomes/microvesicles can be captured onto 15-20 micrometer diameter beads 100 which are also stably trapped within the microfluidic trapping device 12 and can be released into droplets 120 for analysis. These beads 100 can be rigid (e.g., polystyrene, silica, PMMA) or soft (e.g., PEG or polyacrylamide hydrogel). Rigid porous beads 100 or hydrogel beads 100 have advantages in possessing a higher surface area for molecular capture. Beads 100 should have a molecular recognition element coated on their surface (e.g., antibody, aptamer, complementary nucleic acid sequence). Beads 100 can also be given a unique signature or fingerprint: either through size if spherical, shape, fluorescence emission, or absorption-based color, or unique nucleic acid sequences initially introduced on the bead 100 that are incorporated into amplified nucleic acid products as a barcode. Multiple beads of each type (10-20) can then be used where each particular bead contains a recognition element specific to a different target. Bead recognition elements can target circulating tumor DNA (ctDNA) by incorporating a random assortment of cross-sequence complementary nucleic acid strands on the bead or specific nucleic acids complementary to regions of mutations important to select cancer treatments. Alternatively, other DNA binding materials or proteins can be used. Recognition elements can target circulating protein biomarkers as well with antibodies, for example, antibodies to MMPs, or other known biomarkers such as PSA for prostate cancer or CA125 for ovarian cancer. Exosomes can be targeted with antibodies such as anti-CD63, anti-CD81, and anti-EpCAM.

Beads or bead mixtures (with different bead types) are introduced into the blood or other body fluid sample and incubated for 10-30 minutes, or up to an hour under gentle agitation. The blood is then processed on the microfluidic trapping device 12 to isolate any CTCs and/or barcoded beads. Following a wash solution, reagents are flowed through and then beads and cells are released and encapsulated into droplets for downstream assays. Protease assays using peptide targets with FRET paired fluorophores can be used to measure CTC protease secretion or plasma levels of MMPs. Reagents for nucleic acid amplification, e.g., as described for single-cell nucleic acid amplification above, allow for drop-based amplification and e.g., fluorescence detection using intercalating dyes or molecular probes of specific mutations in ctDNA or CTCs. Reagents for protein detection (e.g., antibodies with HRP tag) can be flowed through and washed away while beads are still captured in vortices to yield standard sandwich ELISA based detection in drops using HRP based colorimetric or fluorescence readout in drops. When the assays are complete, droplet fluorescence, color, conductivity, turbidity, etc. can be read out and the bead barcode, or cell fluorescent label can also be read out to yield a multiplexed diagnosis of multiple rare biomarkers present in blood simultaneously. A combination of isolation and analyses on cells (e.g., CTCs) and beads with capture elements for ctDNA or other biomarkers can be used to perform a total liquid biopsy on several circulating biomarker types in a single step.

Figure 11:
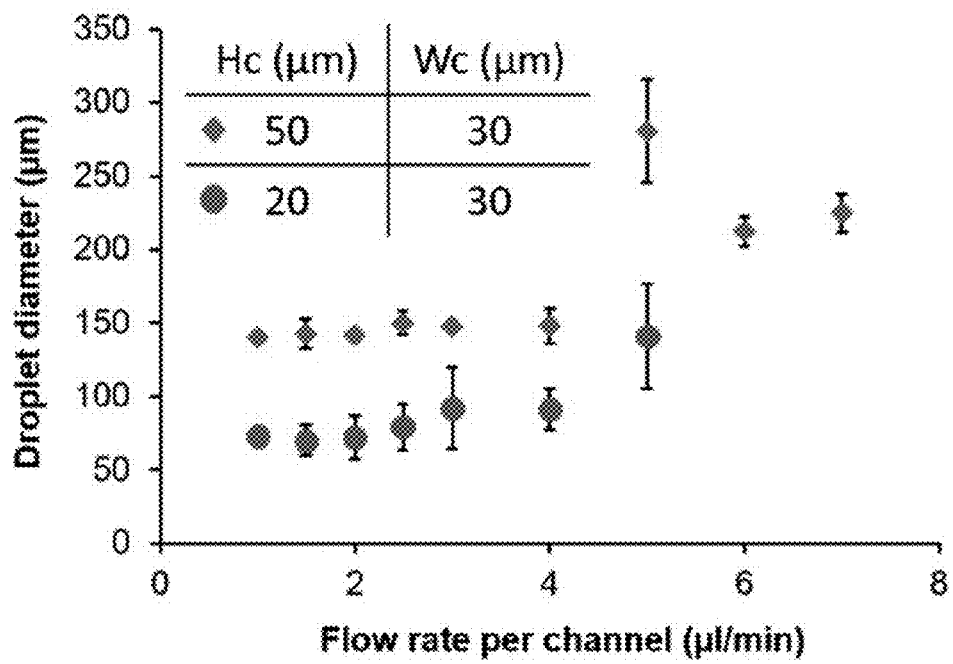
FIG. 11 illustrates data showing how the droplet generation device maintains stable droplet sizes (e.g., between 50-100 μm in diameter) over a range of low flow rates from about 0.5 to 3 μl/min but becomes unstable and polydisperse at higher rates.
Figure 12:
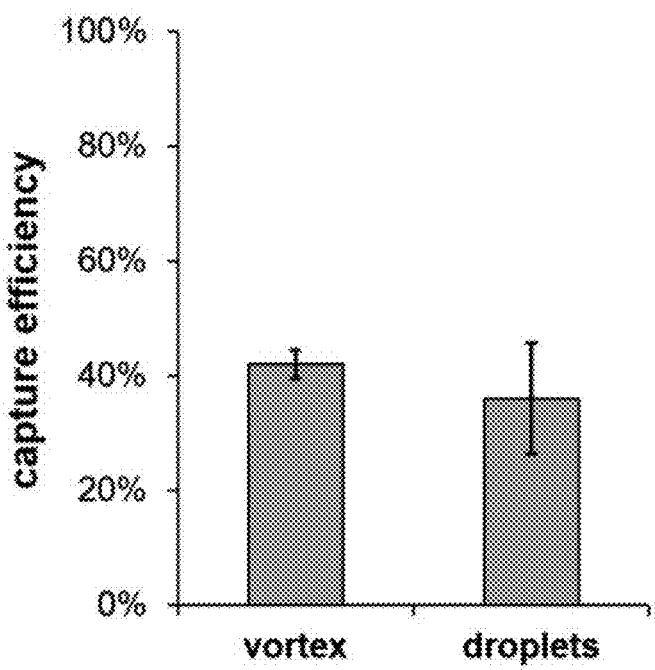
FIG. 12 illustrates the capture efficiency of spiked cells before droplet encapsulation, considering capture in the Vortex HE device and following both Vortex capture and droplet encapsulation.

FIG. 11 illustrates data showing how the droplet generator 14 maintains stable droplet sizes (e.g., between 50-100 μm in diameter) over a range of low flow rates from about 0.5 to 3 μl/min but becomes unstable and polydisperse at higher rates. In addition, higher flow rates result in jetting without recovery. Jetting or continuous connected flow of the aqueous stream is undesirable, since droplets that are regular do not form. It is important to have a droplet generator design that provides relatively uniform size droplets over a range of flow rates, since the release step from the microfluidic trapping device often has variable flow rate. In addition, more uniform sized droplets 120 lead to more uniform reaction conditions for cells or particles and therefore less variation or noise in the downstream assay. Droplets jet at a lower flowrate when channel cross sectional area is smaller. $H_c$ is the channel height and $W_c$ is the channel width of the parallel narrow feed channels. FIG. 12 illustrates the capture efficiency of spiked cells before droplet encapsulation, considering capture in the Vortex HE device and following both Vortex capture and droplet encapsulation.

One particular application of the system is to assay individual circulating tumor cells (CTCs) for the secretion of proteases, which may serve as an improved measure of metastatic potential. Cell-secreted proteolytic enzymes that cleave extracellular matrix (ECM) proteins are implicated in cancer metastasis. Matrix metalloproteases (MMPs) are hypothesized to play a key role in degrading the ECM and enabling extravasation. Analysis of metastatic tumors and patient blood serum has shown significantly higher levels of MMPs, suggesting that CTCs may release MMPs that allow them to degrade the ECM, and that the level of MMPs could serve as a prognostic marker. Measurements of MMP secretion by individual CTCs is necessary, however, this is extremely challenging given the rarity of CTCs and the dilution of few enzymes secreted by single cells into bulk solution. To address these challenges, the integrated system described herein was used to isolate and encapsulate purified cancer cells in blood into a small number of micro-droplets to interrogate MMPs secreted at the single-CTC level for the first time.

A Vortex HE Chip was used as the microfluidic trapping device 12 to isolate CTCs from whole blood at 2.6 mL/min, with 66% purity and 15% efficiency using micro-vortices. Importantly, the vortex device washes out background molecules, and can exchange solution around captured cells, allowing this assay to be highly specific to secretions from captured cells. After CTC isolation and solution exchange with a FRET MMP substrate, captured cells 100 were diverted to a second outlet leading to a droplet generator 14 of the type illustrated in FIG. 6. The droplet generator makes a monolayer of droplets and operates at 1 μl/min per channel with 100 parallel channels, without oil co-flow (an inert oil such as fluorinated oil (e.g., Novec™, 3M along with a surfactant such as Pico-Surf™, Dolomite Microfluidics) is, however, loaded into the droplet generating device). The system is relatively insensitive to changes in flow rate that occur during the release step. Encapsulation increases the concentration of the analyte on the bead or from the cell by $10^5$, which increases the sensitivity of the system. The reaction between protease and substrate occurs inside the droplets 120. Droplets 120 with cells 100 secreting MMPs begin to fluoresce which is detected with an imaging device (e.g., camera used to detect fluorescent droplet). The substrate exhibits low nonspecific signal, because of the integrated solution exchange step. Total analysis from sample input to secretion assay takes minutes (preferably less than 30 minutes), making this system compatible with studying live cells while they retain physiologic conditions. Fluorescent levels can be measured as a proxy for secreted levels of proteases.

The MMP protease assay was performed with live A549 cells. The cells are stained with live cell marker calcein red (1 μg/ml) prior to starting the assay to monitor viability. The amount of active MMP released by each cell in each droplet is measured using a FRET based MMP substrate from AAT Bioquest (Fluorimetric MMP Activity Assay Kit *Green Fluorescence*—Catalog #13510). Initially, the internally quenched FRET peptide substrate is non-fluorescent. Several MMPs (MMP1, MMP2, MMP3, MMP7-14) can cleave the peptide and release two components. One of these components is fluorescent under 544 nm excitation, the other piece is non-fluorescent. The fluorescent increase is proportional to the protease activity.

Figure 13:
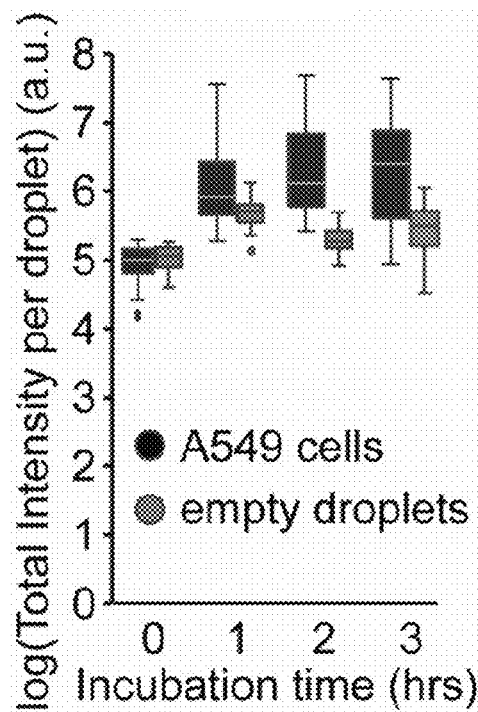
FIG. 13 illustrates a graph of the log (total intensity per droplet) as a function of incubation time.
Figure 14:
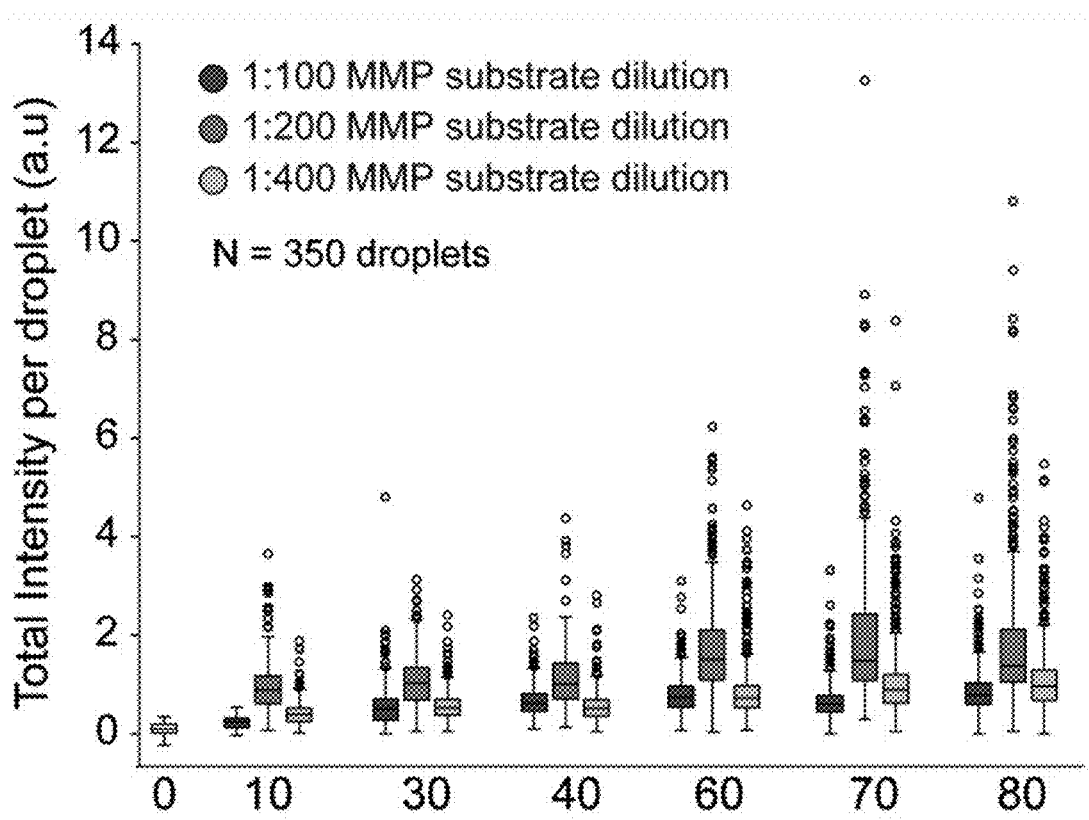
FIG. 14 illustrates a graph of total intensity per droplet as a function of incubation time for different concentrations of MMP substrate. The substrate is functional at concentrations ranging from 1:100 to 1:400 dilution.

FIG. 13 illustrates MMP release and substrate conversion increases over time. Signal increase over time can be measured through fluorescence microscopy, flow cytometry, or imaging cytometry of the droplets 120. Empty droplets 120 do not show signal above the background levels. The substrate is functional at concentrations ranging from 1:100 to 1:400 dilution of stock solution as seen in FIG. 14.

Figure 15:
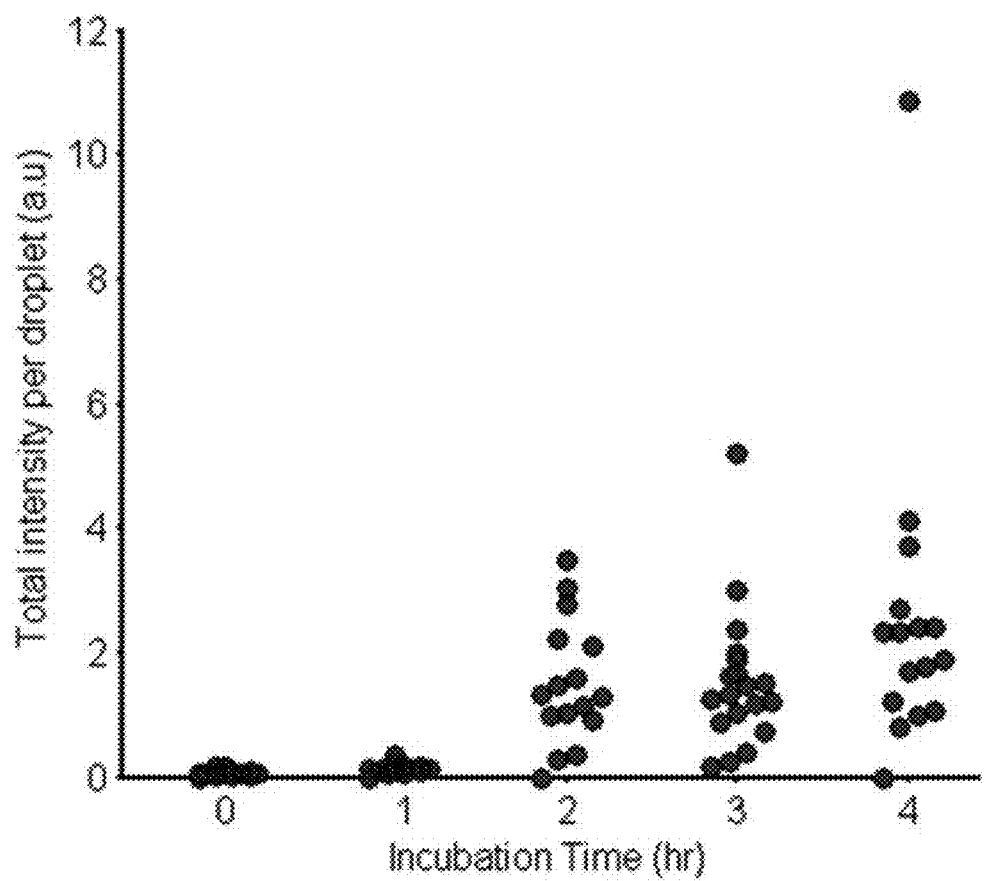
FIG. 15 illustrates the total intensity per droplet as a function of incubation time for another reporter system for serine proteases.

FIG. 15 illustrates the total intensity per droplet 120 as a function of incubation time for another reporter system for serine proteases. Serine proteases released by pancreatic cancer cells (AsPC-1) can also be measured by this system. A fluorogenic peptide based substrate from Thermo Fisher Scientific was used at a concentration of 10 μM. The protease release increases over time as shown over the course of 4 hours.

The ability to purify and encapsulate CTCs in droplets from whole blood opens doors for single CTC nucleic acid mutation detection, genomic or transcriptomic sequencing. These new assays better characterize CTCs enabling improved prognostic measures, and personalized therapy selection based on the mutational profile and heterogeneity of many single-CTCs. For this application, the reagent solution may contain a mixture of reagents to perform nucleic acid amplification and optionally readout. Single-cell whole genome amplification can be performed using several approaches known in the art (e.g., Multiple displacement amplification—MDA, multiple annealing and looping-based amplification cycles—MALBAC), which requires polymerase and amplification buffer mix as well a library of primers. Single cell targeted genome amplification can be performed similarly using more targeted primers to genetic locuses where known druggable mutations are often found. Following amplification, amplified DNA can be collected from the droplet, e.g., by breaking the emulsion for downstream sequencing to identify known and unknown mutations, potential neo-antigens for immunotherapies, and chromosomal abnormalities.

Alternatively, readout directly in the droplets can be performed by using PCR, loop-mediated isothermal amplification, or other nucleic acid amplification approaches with targeted primers, where intercalating dyes or molecular probes are used to measure the amount of amplified DNA directly in each droplet. Primers can be designed to target known mutations in EGFR, HER2, BCR-ABL fusion, ALK translocations, or other druggable genetic lesions. Following amplification for a given time (e.g., 30-40 cycles, or 20 min to 1 hr), the number of highly fluorescent drops above a threshold with cells present can indicate with high specificity the presence of CTCs for prognosis or treatment monitoring. In addition this number can be used to characterize the potential effectiveness of a drug targeting a particular mutation, and provide information to a clinician to prescribe the most efficacious drug.

For most nucleic acid amplification approaches, thermal control is needed to initiate the process of amplification, either at a single temperature or multiple temperatures in a cycle, and this can be conducted while cells 100 are in droplets 120 in the chamber or reservoir 46, or microfuge tube off chip by using surfactants and a controlled high humidity environment to prevent coalescence and evaporation. An example protocol for nucleic acid amplification of single cells in droplets can be found in Kumaresan et al. High-Throughput Single Copy DNA Amplification and Cell Analysis in Engineered Nanoliter Droplets, Anal. Chem. 2008. All PCR solutions are prepared in a UV-treated laminar flow hood (UVP, Upland, Calif.). 100 µL of reaction mix (1× Ampli Taq Gold® buffer with 1.5 mM MgCl2 (Applied Biosystems), 0.2 mM dNTPs (Invitrogen), 1 µg/µL heat inactivated molecular biology grade BSA (Sigma, St. Louis, Mo.), 0.4 ng/µL lambda DNA (New England Biolabs, Boston, Mass.), 0.01% Tween-80 (Sigma), 0.4 µM forward and 0.04 µM reverse primers, 0.4 U/µL Ampli Taq Gold® Polymerase (Applied Biosystems)) is prepared in a 0.6 mL PCR tube. The reaction mix is stored on ice and the polymerase is added right before processing. The reaction mix acts as the reagent solution that is introduced around the cells trapped in the microfluidic device. After release of cells and droplet collection, the droplets are thermocycled as follows: 10 min at 95° C.—hotstart initiation, 40× (30 s at 95° C., 90 s at 55° C., 60 s at 72° C.)—amplification, 7 min at 72° C.—final extension.

The 10 min hot start step for polymerase activation at the beginning of PCR also serves to completely lyse the cells and release the genomic DNA into the droplet volume. Alternatively, lysis can be performed chemically while cells remain trapped in the microfluidic device using a weak lysis/permeabilization wash solution (e.g., lysis buffer (100 mM Tris pH 8.0, 0.2% Tween-20, proteinase K 1.5 mg/ml), followed by introduction of a nucleic acid amplification solution, and then droplet generation. Weak lysis still leads to an overall intact cell structure (without cells being lost from the microfluidic trap) and with the larger genomic DNA remaining trapped in this structure and available. In this approach smaller molecules within the cell and lysis reagents that interfere with nucleic acid amplification are washed away prior to encapsulation and downstream reaction in the droplets. Beyond nucleic acid sequence analysis, measurement of epigenetic marks on DNA and histones can also be performed using the above described approaches (e.g., using ATAC-seq, ChIP-seq, etc.).

In addition, the ability to collect molecules from blood onto a large bead, wash background molecules away, and compartmentalize the beads in a highly multiplexed manner for downstream analysis, highly concentrated in a drop, enables a range of biomarkers to be read from blood, including nucleic acids, proteins, and exosomes/microvesicles. In such a method, beads may be incubated with blood or a blood fraction (or other bodily fluid) "off-chip" and then run through the system as described herein. These biomarkers combined, or also in combination with CTCs isolated with the same platform can provide a more complete picture of a patient's cancer state and personalized therapies that can be given (i.e., a total liquid biopsy).

Experimental—Measuring MMP Secretion by Individual CTCs

Measuring MMP secretion by individual CTCs is extremely challenging given the rarity of CTCs and the dilution of the few enzymes secreted by single cells into bulk solution. Current techniques that enable measurement of single-cell secretions confine cells into a small volume of surrounding fluid using microwells or droplet microfluidics. By confining the secretions to a small volume both techniques increase the concentration of the secreted analyte by orders of magnitude, which increases the sensitivity of the analysis. However, current microwell and drop-generating systems are not integrated with purification or solution exchange operations necessary to measure secretions of individual cells without background contamination or significant cell loss in transfer steps. In addition, current droplet generators are complex requiring multiple pumps and precise control of flow rates. Although microwell approaches can be used to confine individual cells to small volumes, droplet-generating systems have additional functionality that allows downstream sorting based on a secretion profile with established techniques such as Fluorescent Activated Droplet Sorting.

Two main classes of microdroplet generators are available for single-cell encapsulation: (1) an aqueous/oil co-flow geometry where droplet size depends on flow rate and (2) step emulsification designs where droplet size has been shown to be less dependent on flow rate, making them more amenable to integration. Flow focusing droplet generators have been used to encapsulate immortalized cancer cells and isolated leukocytes to measure protease production. Jing et al., "Single Cell Analysis of Leukocyte Protease Activity Using Integrated Continuous-Flow Microfluidics." Analytical Chemistry (2016) highlight the importance of completely washing out background proteases in media or plasma around cells to obtain a cell-specific signal without substantial background fluorescence. The device of Jing et al. achieves washing by transitioning a stream of sample with leukocytes into a reaction buffer using deterministic lateral displacement (DLD). The droplet generator junction is located downstream of the reaction buffer channel. Due to the continuous generation of droplets, however, a large number of empty droplets are made during the entire sample processing time. In a rare cell analysis system, a small percentage of these droplets would have cells in them which would lead to longer imaging and analysis times. These droplet platforms are compatible with cell lines and experiments with large numbers of cells; however, they are difficult to adopt for analyzing CTCs in large volumes of clinical blood samples with huge numbers of background cells. In order to study protease release by CTCs, an integrated system that can isolate CTCs from blood, wash away contaminating blood cells and plasma, introduce new reagents, and encapsulate them into droplets without manual transfer steps is required. Such an integrated and rapid processing system is also important to minimize the time from blood draw to readout to preserve the physiological state of cells as in the blood.

The system 10 described herein combines vortex trapping of rare circulating tumor cells by size and deformability and a novel extreme throughput droplet generator to measure proteases secreted by individual cells. CTCs are trapped in the microfluidic trapping device as described herein. Larger cells, such as CTCs, are stably trapped within the microvortices that form in the expansion regions, while smaller red and white blood cells enter but do not form stable limit cycles or orbits. Upon trapping, solutions are exchange around the CTCs while under continuous flow to wash out plasma proteins and leave pure cells within a continuously exchanging reaction buffer (fluorogenic MMP-cleavable peptide substrate), reducing any nonspecific signals. The trapped CTC cells are released into an inline connected droplet generator where they are encapsulated into uniform droplets without any manual transfer steps. In these steps 20 ml of diluted blood volume is reduced down to a few hundred microliters. Thus the captured cells are isolated in a smaller number of droplets (<50,000), reducing the analysis time. The droplet generator is designed to yield minimal dependence of drop diameter on flow rate, and is also parallelized to be compatible with the higher flow rates of the release step from the microfluidic trapping device.

After cells are encapsulated into droplets with MMP-cleavable peptide substrate, the drops are incubated to accumulate secreted proteases and the fluorescent reaction products of peptide cleavage. The fluorescent intensity in each droplet is then analyzed using a fluorescent microscope and/or an inflow high speed fluorescent imaging system which correlates intensity in droplets to intensity of other cellular markers of each encapsulated cells. This approach allows one to rapidly accumulate large quantities of signal and investigate single-cell secretions of proteases from CTCs with high confidence, and is amenable to other single-cell secretion, genomic and proteomic analyses on single-CTCs with a seamless workflow.

Methods—Assay Operation

Prior to CTC isolation whole blood samples were stained directly in EDTA collection tubes to identify subpopulation of cells. For every 6 mL of whole blood 104 CD45-PE (BD Bioscience cat #555483), 10 µL CD66c-PE (eBioscience cat #12-0667-41), 10 µL PSMA-APC (Miltenyi Biotec cat #130-106-609), and 6 µL of 50 µg/mL Hoechst (Thermo Fisher H3570) was used. Whole blood was stained in the dark at room temperature for 30 minutes.

After staining, the stained blood was diluted 20× in filtered PBS immediately before processing through the microfluidic trapping device (i.e., Vortex HE chip). The Vortex HE chip isolates CTCs from whole blood at 2.6 mL/min. During CTC isolation the wash buffer and MMP peptide substrate solution runs at 0.3 mL/min and the sample runs at 2 ml/min all controlled using syringe pumps (Harvard Apparatus), although pressure sources can also be used to drive flow. When using syringe pumps, the wash and substrate solutions need to be operated in infuse mode to prevent blood backflow into the solutions. When using pressure driven flow, positive pressures would need to be applied to each of these reservoirs to drive the desired flow. These flow rates were optimized for 20 mL BD plastic pack syringes, processed on Harvard apparatus syringe pump (cat #71-2001). CTCs and other large cells are isolated in vortices at these flow rates, while smaller cells such as red and white blood cells flow to a first waste reservoir.

After CTC trapping in vortices, the device is switched to new flow conditions. The solution is exchanged to the PBS wash buffer which washes out background molecules while maintaining trapped cells. While the wash buffer is infused at 2.4 ml/min the sample withdraws simultaneously at a low flow rate of 0.1 ml/min. The sample withdraw prevents remaining blood from infusing into the microfluidic trapping device and contaminating the signal with additional proteases or non-CTC cells. After a one (1) minute wash, the wash buffer flow is stopped, and the substrate flow is switched to 2.7 ml/min, this second solution change introduces the peptide substrate. After four (4) seconds the vortices fill with the substrate solution, all while maintaining trapped larger cells circulating within the vortices. The time required to completely fill the vortices was determined from high speed imaging of trypan blue as a contrast agent in the vortex chambers. The substrate is a peptide sequence with a FRET (Fluorescence Resonance Energy Transfer) pair in which the peptide is a target of broad spectrum MMP activity (AAT Bioquest cat #13510); it is specific for eleven (11) different MMPs. The substrate was used at 1 to 200 dilution in RPMI base media. For all MMP9 specific experiments, a different peptide FRET substrate was used from Biozyme (cat # PEPDAB052m001) at 10 µM in RPMI.

Figure 16:
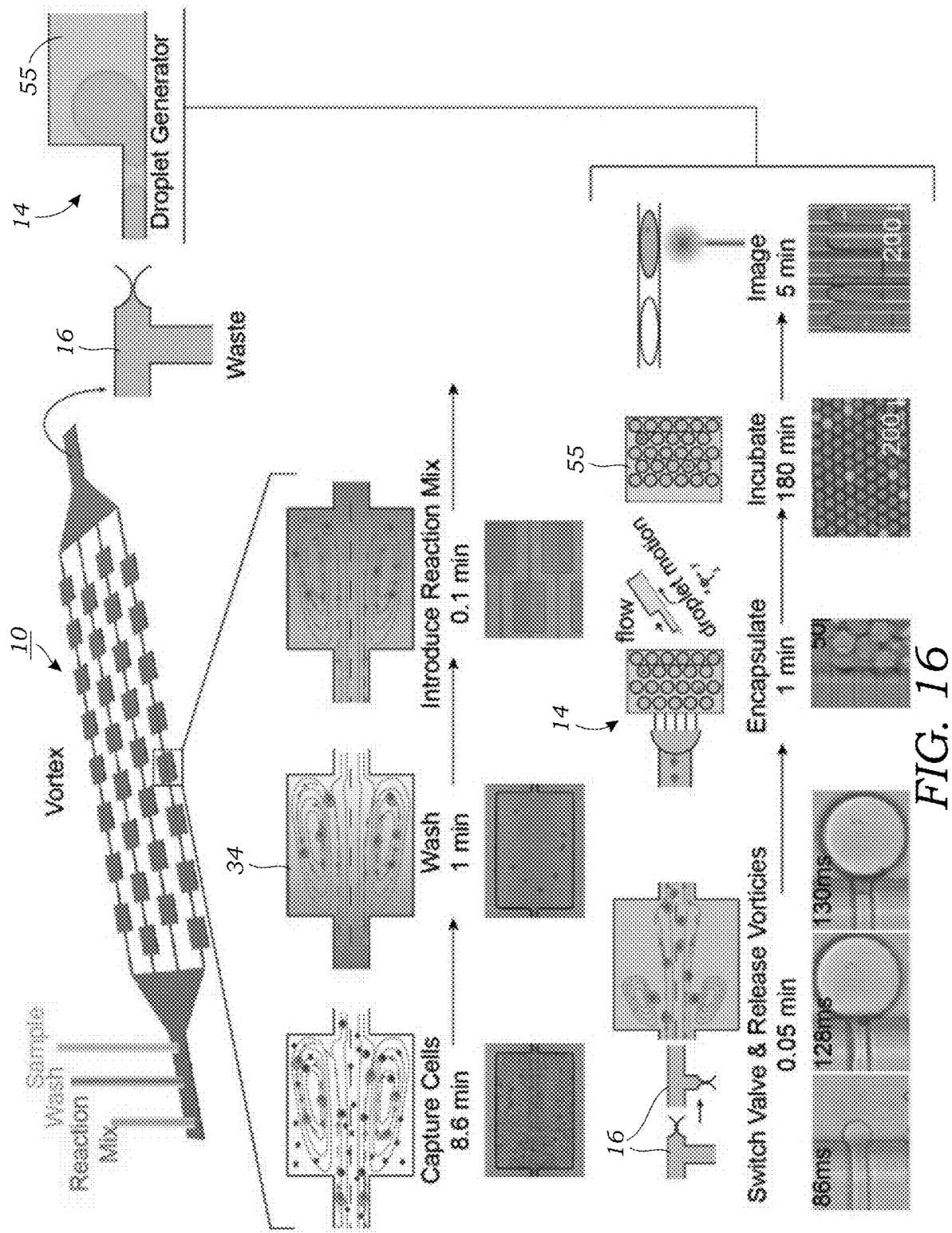
FIG. 16 illustrates a schematic illustration of the sequence of steps or operations used to capture and encapsulate CTCs followed by imaging.

Once the substrate replaces all the solution around the cells, the first waste outlet is closed with a valve and the flow is diverted to the second outlet of the pinch valve leading to a droplet generator. The pinch valve has two output tubes, one is normally pinched in the off position while the other is open. The input of the droplet generator connects to the normally off tube, while the second tube goes to the waste outlet. When the valve receives 24V input, the switch alters the pinch position such that the output from the Vortex chip goes to the droplet generator device, and the waste tube is pinched off. The vortices are then dissipated by stopping flow to the sample syringe and lowering the substrate flow to 0.05 ml/min. At this flow rate vortices decay and cells are released in the new substrate solution to the droplet generator device. This release step runs for about 10-15 seconds, while the cells get encapsulated into droplets in the step emulsification-based droplet generator with an attached oil reservoir. The step emulsifier that was used was highly parallelized with one-hundred (100) channels, which allows it to operate at very high flow rates, while maintaining a lower flow rate per channel such that flow does not jet but instead forms monodisperse drops. Initially the droplet generator reservoir is 50% full with 0.5% Pico-Surf™ (Sphere Fluidics, cat # SF-000149) in Novec™ 7500 (3M, cat #9802122937), and the device is held at a ~90 degree angle relative to horizontal to allow buoyant droplets to move up and away from the inlet region and allow more droplets to form at the step junction of the droplet generator device. After the encapsulation process the droplet generation device is filled completely with the 0.5% Pico-Surf™ in Novec™ 7500 and oriented at about 90° relative to horizontal (i.e., the droplet generation device is oriented in a vertical manner). This allows the droplets to form a monolayer and the accumulation of signal over 30 min to 3 hr, and even up to 6 hr. The sequence of steps or operations used to capture and encapsulate CTCs followed by imaging is seen in FIG. 16.

The reaction between the protease and the substrate occurs inside the droplets for more than one hour (e.g., three (3) hours preferably). After this incubation step the droplets are then imaged in the reservoir. Imaging for all cell line experiments was done using the Axio Observer Z1 Zeiss fluorescent microscope, all imaging for the clinical samples were done using a Nikon fluorescent microscope. Both microscopes used Nikon CoolSnap HQ2 cameras. The substrate fluoresces in the FITC channel and was imaged with a 400 ms exposure. An image processing algorithm was used to detect the boundary of the droplets in brightfield and calculate the intensity of the cleaved MMP substrate peptides in the FITC channel which accumulates in each droplet. Droplets with specific cells in them were identified based on staining of cell-specific markers for leukocytes and cancer cells in other fluorescent channels before calculating secretion content.

Device Fabrication

Devices were made with the polymer polydimethylsiloxane (PDMS) using replica molding. The Vortex HE microfluidic trapping device is fabricated using a mold structure on a 4 inch silicon wafer (University Wafer Inc.) by photolithograpy. KMPR 1050 (Microchem) was spin coated to form the microchannel features. The PDMS device was made with Sylgard 184 Elastomer (Dow Corning Corporation) with a cross-linker to polymer ratio of 1:10, and cured at 60° C. for 21 h. The devices were cut from the mold, and entry ports were punched using a 1.5 mm TiN coated biopsy needle (Syneo, LLC). The PDMS layer and a glass slide (VWR International, LLC) were $O_2$ plasma treated (Oxford Technics RIE) for 30 s, at 500 mTorr, 80 W power before being bonded together to enclose the microchannels.

The droplet generator is fabricated using double layer photolithography. The mold structure was fabricated on a 4 inch silicon wafer (University Wafer Inc.) by photolithograpy. For the first layer containing the channels, KMPR 1050 (Microchem) was spun coated with spin speed of 3500 rpm, ramped at 300 rpm/s for 30 s for 50 µm heights and 30 µm widths and 1000 µm lengths. Devices were soft baked for 15 minutes at 100° C. and cooled for 5 minutes. The exposure time was 120 s at 8.5 W power. The devices where then post-exposure baked for 3 minutes at 100° C. The devices were cooled for 5 minutes on metal cooling bench. The second layer of KMPR was spun at 900 rpm ramped at 300 rpm/s for 30 s, soft baked for 20 minutes. The wafer was cooled for 5 minutes and a third layer of KMPR was poured and previous step was repeated. The wafer was then protected from light and cooled for at least 15 hours at room temperature. The masks were aligned using alignment marks and the wafer was exposed for 200 s. The post exposure bake was done for 10 min. The wafer was cooled for 5 minutes, and developed using SU-8 developer. The container with the wafer and developer was put in a sonicator for 2 minutes, removed and unexposed photoresist was removed by agitation. The reservoirs had a height 500 µm-1000 µm. Device features were measured with a Dektak profilometer. The PDMS droplet generator device was made with Sylgard 184 Elastomer (Dow Corning Corporation) with a cross-linker to polymer ratio of 1:10, and cured at 60° C. for 21 hours. The devices were cut from the mold, and entry ports were punched using a 1.5 mm biopsy needle (Integra Miltex cat #33-38). The PDMS layer and a glass slide (VWR International, LLC) were $O_2$ plasma treated (Oxford Technics RIE) (for 30 seconds, at 500 mTorr, 80 W power before being bonded together to enclose the microchannels.

Figure 17:
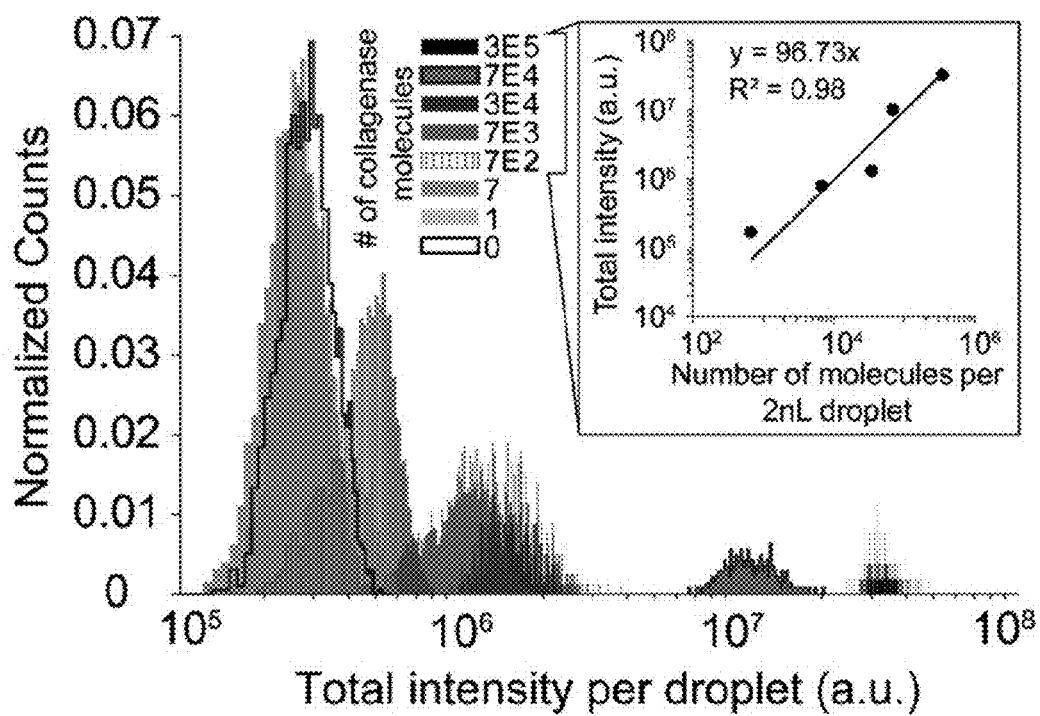
FIG. 17 illustrates a graph of the total intensity per droplet (a.u.) as a function of the number of molecules per droplet to test the detection limits of the assay using serial dilutions of known concentrations of collagenase.
Figure 18:
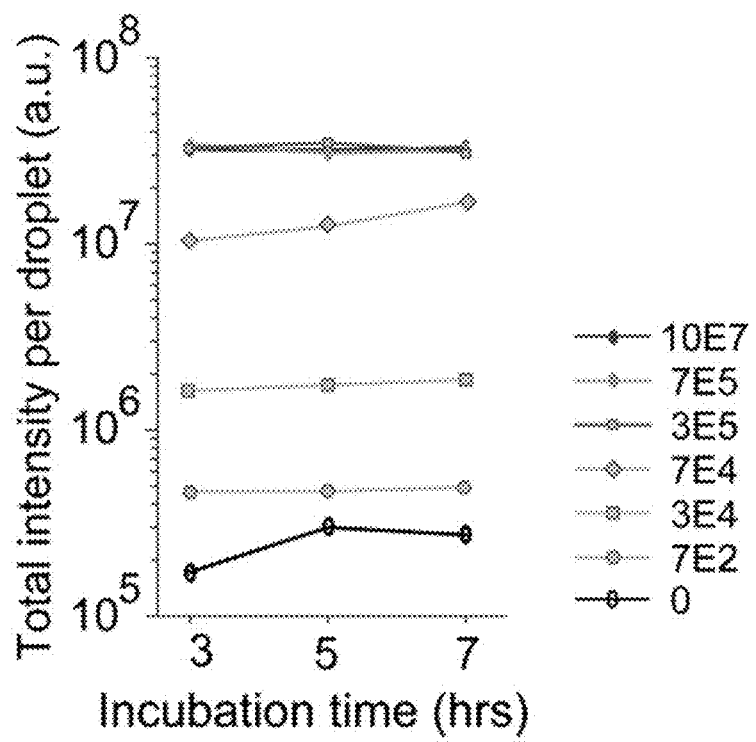
FIG. 18 is a graph of total intensity per droplet (a.u.) as a function of incubation time (hrs.) for collagenase.

FIG. 17 illustrates a graph of total intensity per droplet (a.u.) as a function of number of molecules per droplet to test the detection limits of the assay using serial dilutions of known concentrations of collagenase. Poisson loading of droplets was found to occur at low concentrations where most droplets are empty and a few have enough collagenase to generate a signal. A linear correlation exists between droplet intensity and number of molecules reacted for greater than 700 molecules per droplet. These correlations can be used to extrapolate the minimal number of molecules secreted by single cells. These results indicate that there is a large dynamic range of detection. FIG. 18 is a graph of total intensity per droplet (a.u.) as a function of incubation time (hrs.) for collagenase. The assay can clearly distinguish between hundreds to ten thousands of collagenase molecules. The signal becomes indistinguishable and saturated for concentrations of greater than 100,000 per droplet.

Figure 19:
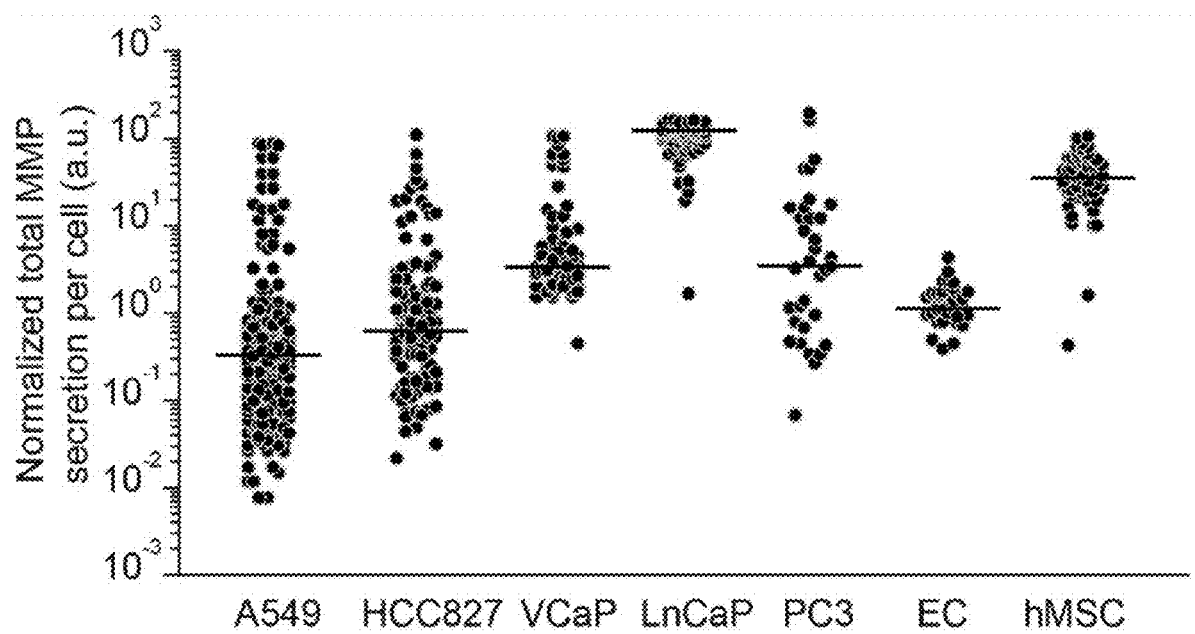
FIG. 19 illustrates measured MMP secretion levels for different cell lines. Lung cancer cell lines (A549, HCC827), prostate cancer cell lines (VCaP, LnCaP, and PC3) as well as endothelial cells and mesenchymal stem cells secrete varying levels of MMPs.

FIG. 19 illustrates measured MMP secretion levels for different cell lines. Lung cancer cell lines (A549, HCC827), prostate cancer cell lines (VCaP, LnCaP, and PC3) as well as endothelial cells and mesenchymal stem cells secrete varying levels of MMPs. These cells were also stained with CellTracker™ dyes to distinguish cell viability. Only droplets with single viable cells were measured. Cells that were dying had fluorescent CellTracker™ leak out into the surrounding droplet and these results were discarded. The empty droplets were used as an internal negative control. A large variation at the single-cell level within a cell line was observed.

Figure 20:
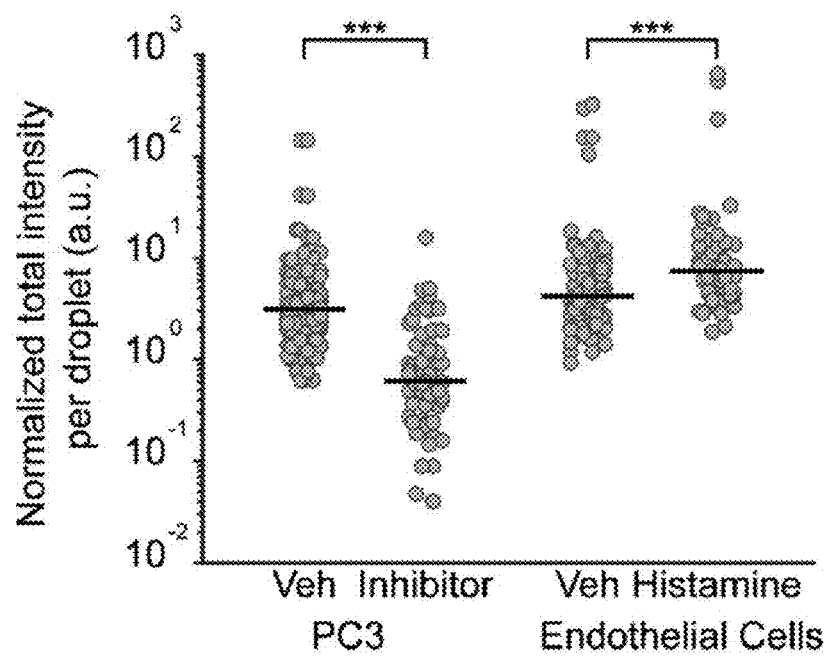
FIG. 20 illustrates a graph of normalized total intensity per droplet (a.u.) for PC3 prostate cancer cells with the application of secretion inhibitors brefeldin and monensin and endothelial cells with the application of MMP upregulator histamine. Veh is vehicle control; no drugs were applied to this set. Inhibitor set refers to set in which drugs were applied to cells.

FIG. 20 illustrates a graph of normalized total intensity per droplet (a.u.) for PC3 prostate cancer cells with the application of secretion inhibitors brefeldin and monensin and endothelial cells with the application of MMP upregulator histamine. Monensin and brefeldin together sequester proteins in the golgi apparatus and prevent them from being secreted. As expected, there is a decrease in secretion in the presence of the inhibitors. Histamine stimulates MMP secretion in endothelial cells and as expected; there is an increase in secretion in the presence of histamine.

Figure 21:
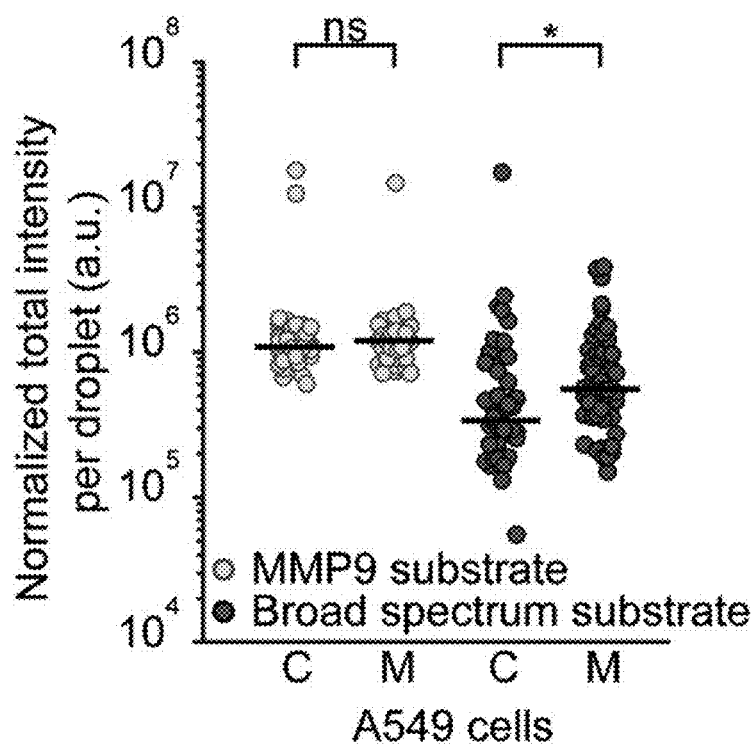
FIG. 21 illustrates a graph of normalized total intensity per droplet (a.u.) for control, not mutated cells (C) and cells mutated for SNAIL over expression (M).

FIG. 21 illustrates a graph of normalized total intensity per droplet (a.u.) for control, not mutated cells (C) and cells mutated for SNAIL over expression (M). The assay was studied for the effects on MMP9 and broad spectrum MMP secretion in wild-type A549 lung cancer cells (C) and A549 cells overexpressing SNAIL, a transcription factor involved in epithelial to mesenchymal transition (EMT). There is a significant increase in signal from a peptide substrate cleaved by a broad spectrum of MMPs in SNAIL overexpressing cells, indicating these cells secrete higher levels of MMPs, although not MMP9. SNAIL overexpression is indicative of the epithelial to mesenchymal transition that is thought to occur in more metastatic cancer cells.

Figure 22:
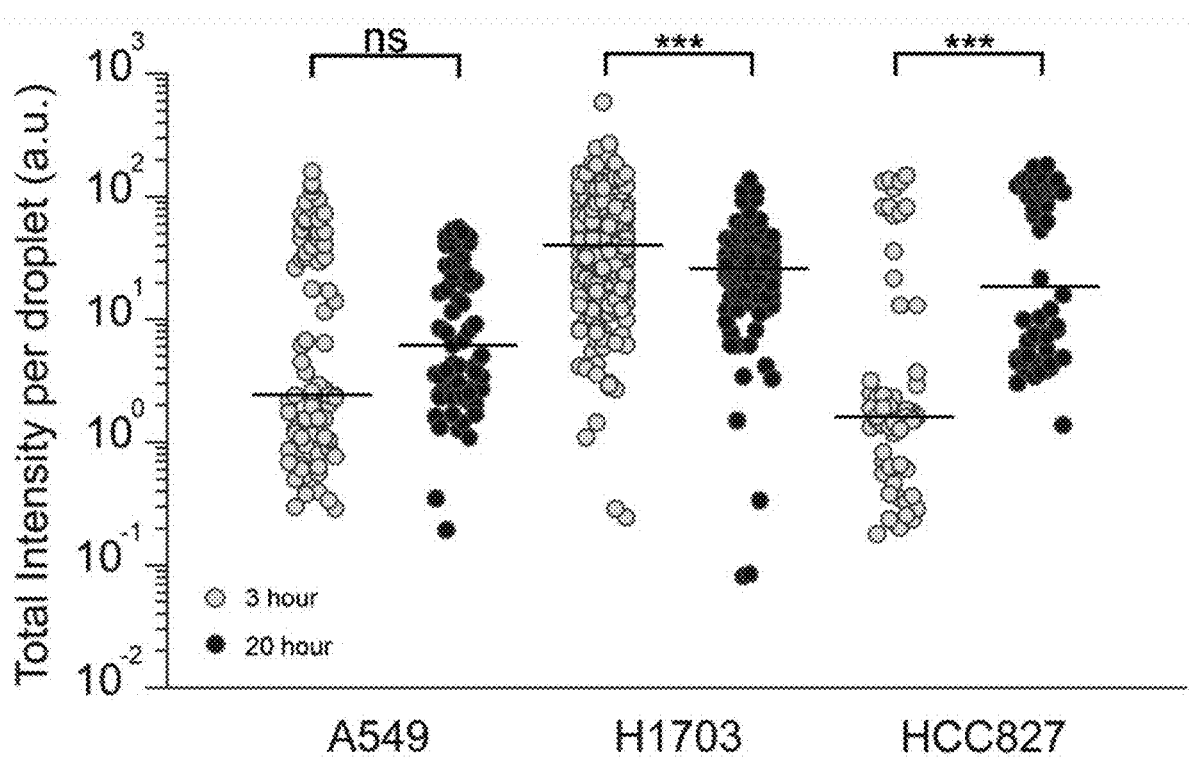
FIG. 22 illustrates a graph of total intensity per droplet (a.u.) for lung cancer cells interrogated for MMP secretion at 37° C. for 3 hours and 20 hours.

FIG. 22 illustrates a graph of total intensity per droplet (a.u.) for lung cancer cells interrogated for MMP secretion at 37° C. for 3 hours and 20 hours. There is no significant difference in secretion over this time frame for A549 cells. However H1703 and HCC827 have some significant differences in secretion over a longer period of time.

Figure 23:
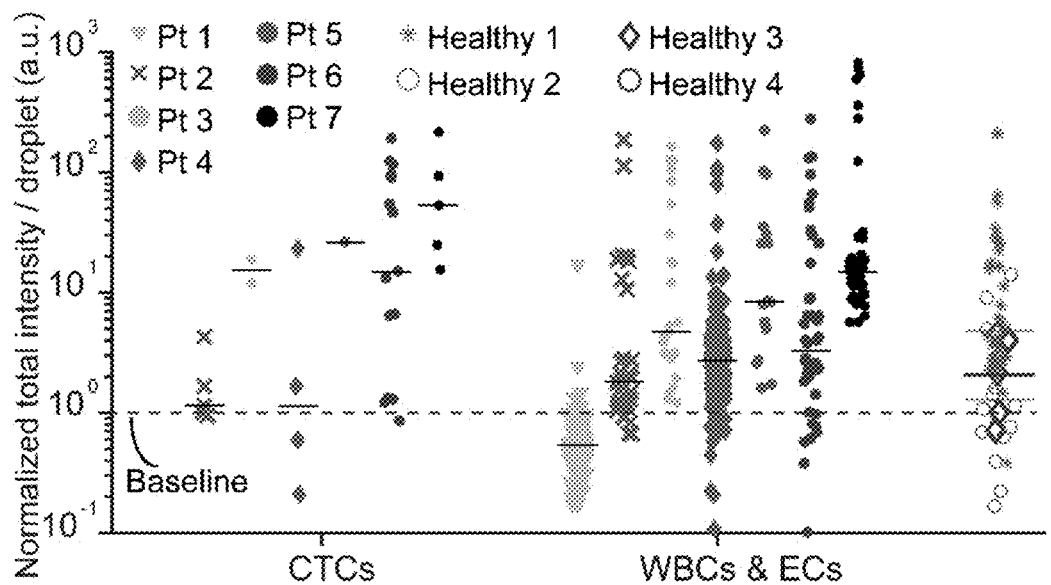
FIG. 23 illustrates a graph of normalized total intensity per droplet for CTCs, WBCs, and ECs obtained from blood samples from prostate cancer patients and healthy volunteers that were processed to determine MMP secretion from captured cells encapsulated in droplets using the system described herein.

Blood samples from prostate cancer patients and healthy volunteers were processed to determine MMP secretion from captured cells encapsulated in droplets using the system described herein. FIG. 23 illustrates a graph of normalized total intensity per droplet for CTCs, WBCs, and ECs for the above-noted patients. Mean intensity for each patient dataset is indicated by the short, solid line. Cells in blood were stained with anti-prostate specific membrane antigen (anti-PSMA), DAPI, anti-CD31, anti-CD66c, and anti-CD45 to distinguish CTCs from white blood cells (WBCs) and endothelial cells (ECs). Cells that are negative for CD31 and CD45, positive for PSMA or had a large nucleus were classified as CTCs. Six (6) out of seven (7) patient samples were observed to have CTCs. Each of these samples had CTCs with above baseline levels of MMP secretion. Baseline, in the context of FIG. 23, is defined as the mean intensity of empty droplets (i.e., dashed line in FIG. 23). Empty droplets were used as an internal negative control and used to normalize the intensity of droplets containing cells. Thus, for FIG. 23, droplets with intensity levels above the baseline value of "1" are deemed to have a positive signal. A somewhat positive correlation is seen between the highest observed levels of MMPs secreted by CTCs and the highest observed levels of MMPs secreted by WBCs and ECs. That is to say, for example, if the observed highest level of MMPs in CTCs for a particular patient is low it is likely that the observed highest level of MMPs for WBCs and ECs will also be low. Conversely, if the observed highest level of MMPs in CTCs for a particular patient is high it is likely that the observed highest level of MMPs for WBCs and ECs will also be high. Interestingly, the sample with the lowest level of MMP secretion in WBCs and EC (Pt 1) had no CTCs and corresponded to a patient with no new metastasis or radiographic progression. These data indicate that levels of MMPs secreted by circulating cells may be predictive of disease state.

In-Situ PCR

In addition to measuring proteases of isolated cells in droplets, the system described herein may also be used to pre-treat cells for other downstream molecular assays. Trapped cells can be fixed and permeabilized in flow in the microvortices. An in-flow cell treatment reduces the number of centrifugation and wash steps necessary for performing the same procedures on cells in well plates. Cell treatment in flow reduces the number of steps in downstream assays such as immunostaining and in-situ PCR. Here the system is used for in-situ PCR, particularly because finding mutations in rare CTCs is difficult in established well plate based systems. The integrated system described herein can be adapted to pretreat target cells while circulating in microvortices and then encapsulating them into droplets for PCR, DNA or RNA sequencing.

Past work on in-situ PCR has established the requirements for gaining access to the cellular DNA. The cell membrane and the nuclear membrane needs to be permeabilized to allow primers and polymerases to enter the cell. In addition, proteins such as histones bound to DNA should be removed to allow access to nucleic acids. Paraformaldehyde (PFA) and proteinase K must be removed to allow the following nucleic acid amplification steps to proceed. In this system, this initial step of exposure and removal is achieved while captured cells are circulating in microvortices by exchanging solutions to first a PFA solution, and then proteinase K and/or surfactant solutions such as sodium dodecyl sulfate (SDS). Once the primers and polymerase gain access into the nucleus, thermocycling initiates amplification. DNA intercalating dye such as SYBR® green or EvaGreen® can be added and indicates if amplification occurred. These methods were used to successfully detect K-ras mutation in cells.

Figure 24:
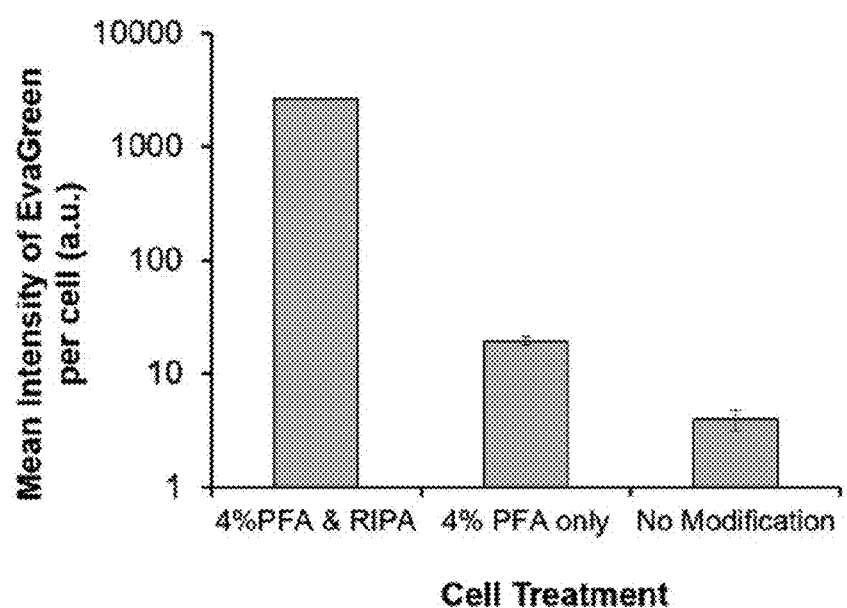
FIG. 24 illustrates a graph of the mean intensity of EvaGreen® per cell (a.u.) for different cell treatments (4% PFA & RIPA, 4% PFA only, no modification) while cells were maintained circulating in microvortices on a chip.

Experiments were conducted to treat cells in microvortices formed using the microfluidic trapping device discussed herein. The device remains the same as for the assay for MMP measurement. The wash buffer is substituted with the fixative 4% PFA, permeabilization agents RIPA buffer and proteinase K. A 50:50 volume fraction of PFA and RIPA buffer was used. These reagents open the cell membrane enough to allow large molecules to enter the cell and create access to DNA in the nucleus. The reaction mix for amplification is in a separate third inlet. The sample inlet of cells remains the same. After treatment of cells in vortices, the degree of access to DNA was characterized using 34 Evagreen® (Biotium) and 0.005 mg/ml of DAPI (Molecular Probes) stains to characterize the process for making DNA accessible. The intensity of EvaGreen® in the nucleus was found to increase over two orders of magnitude upon exposure to PFA followed by RIPA buffer. FIG. 24 illustrates the mean intensity of EvaGreen® per cell (a.u.) for different cell treatments. Importantly and unexpectedly, cells are not completely degraded during the process of exposure to surfactants such as RIPA, such that cells can remain gently circulating within the vortices even when adding reagents that are known to lyse cells. This is important to allow solutions to be exchanged again to a wash and/or an amplification buffer around circulating cells. Lysis and amplification solutions are incompatible and require complete solution exchange.

Following the permeabilization process performed on cells circulating in microvortices reagents for PCR amplification or whole genome amplification (WGA) of cells can be added and cells can be encapsulated in droplets with these reagents for amplification using the droplet generation device. Single-cell PCR or WGA in droplets enables a reduction in background from wild-type cells that may also be captured, as well as single-cell level characterization of heterogeneity in genomic mutations or RNA expression levels.

While embodiments of the present invention have been shown and described, various modifications may be made without departing from the scope of the present invention. The invention, therefore, should not be limited except to the following claims and their equivalents.

What is claimed is:

1. A system for isolating and emulsifying particles or cells within droplets comprising:
   a microfluidic trapping device having an inlet and an outlet and one or more channels disposed between the inlet and the outlet, at least some of the one or more channels having a plurality of expansion regions serially arranged along the length thereof;
   a droplet generation device fluidically coupled to the outlet of the microfluidic trapping device, the droplet generation device comprising a plurality of channels of a first height that terminate at an interface into a chamber having a second height that is greater than the first height, wherein the plurality of channels of the droplet generation device and the chamber contain an oil phase therein.

2. The system of claim 1, wherein the number of the plurality of channels in the droplet generation device is between about 50 and about 200.

3. The system of claim 1, further comprising one or more pumps fluidically coupled to the inlet of the microfluidic trapping device.

4. The system of claim 3, wherein the one or more pumps are coupled to a sample source, wash source, and reactant or reagent source.

5. The system of claim 1, further comprising a valve interposed between the outlet of the microfluidic trapping device and an inlet of the droplet generation device, the valve having a first outlet leading to the droplet generation device and a second outlet leading to a waste stream or reservoir.

6. The system of claim 1, further comprising an imaging device configured to image droplets from the droplet generation device.

7. The system of claim 1, wherein the first height is about 30-50 µm and the second height is about 200 µm.

8. The system of claim 1, wherein the droplet generation device is angled relative to horizontal.

9. The system of claim 1, wherein the droplet generation device is angled within the range of about 30° to about 90° relative to horizontal.

10. The system of claim 1, wherein the chamber of the droplet generation device comprises an upper surface or roof that maintains a substantially uniform height across the chamber.

11. The system of claim 1, wherein the interface comprises a step junction.

12. The system of claim 1, wherein the chamber contain an oil phase and surfactant mixture therein.

* * * * *